(12) United States Patent
Hinrichs et al.

(10) Patent No.: US 12,187,779 B2
(45) Date of Patent: *Jan. 7, 2025

(54) ANTI-HUMAN PAPILLOMAVIRUS 16 E6 T CELL RECEPTORS

(71) Applicant: The United States of America, as represented by the Secretary, Department of Health and Human Services, Bethesda, MD (US)

(72) Inventors: Christian S. Hinrichs, Princeton, NJ (US); Steven A. Rosenberg, Potomac, MD (US)

(73) Assignee: The United States of America, as represented by the Secretary, Department of Health and Human Servces, Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/323,493

(22) Filed: May 25, 2023

(65) Prior Publication Data

US 2023/0340066 A1 Oct. 26, 2023

Related U.S. Application Data

(63) Continuation of application No. 17/142,486, filed on Jan. 6, 2021, now Pat. No. 11,697,676, which is a continuation of application No. 16/408,939, filed on May 10, 2019, now Pat. No. 10,913,785, which is a continuation of application No. 15/786,966, filed on Oct. 18, 2017, now Pat. No. 10,329,339, which is a continuation of application No. 14/905,108, filed as application No. PCT/US2014/046480 on Jul. 14, 2014, now Pat. No. 9,822,162.

(60) Provisional application No. 61/846,167, filed on Jul. 15, 2013.

(51) Int. Cl.
| | |
|---|---|
| *A61K 39/12* | (2006.01) |
| *A61K 39/00* | (2006.01) |
| *C07K 14/725* | (2006.01) |
| *C07K 16/28* | (2006.01) |
| *G01N 33/566* | (2006.01) |
| *A61K 38/00* | (2006.01) |

(52) U.S. Cl.
CPC ...... *C07K 14/7051* (2013.01); *A61K 39/4611* (2023.05); *A61K 39/4632* (2023.05); *A61K 39/464491* (2023.05); *A61K 39/464838* (2023.05); *C07K 16/2809* (2013.01); *G01N 33/566* (2013.01); *A61K 38/00* (2013.01); *C07K 2317/34* (2013.01); *C07K 2319/00* (2013.01); *G01N 2333/7051* (2013.01); *G01N 2800/7028* (2013.01)

(58) Field of Classification Search
None
See application file for complete search history.

(56) References Cited

U.S. PATENT DOCUMENTS

| | | |
|---|---|---|
| 5,087,616 A | 2/1992 | Myers et al. |
| 5,225,539 A | 7/1993 | Winter |
| 5,449,752 A | 9/1995 | Fujii et al. |
| 5,545,806 A | 8/1996 | Lonberg et al. |
| 5,569,825 A | 10/1996 | Lonberg et al. |
| 5,585,089 A | 12/1996 | Queen et al. |
| 5,639,641 A | 6/1997 | Pedersen et al. |
| 5,693,761 A | 12/1997 | Queen et al. |
| 5,714,352 A | 2/1998 | Jakobobits et al. |
| 6,265,150 B1 | 7/2001 | Terstappen et al. |
| 8,034,334 B2 | 10/2011 | Dudley et al. |
| 8,383,099 B2 | 2/2013 | Dudley et al. |
| 10,143,724 B2 | 12/2018 | Morgan et al. |
| 2002/0197266 A1 | 12/2002 | Sasso |
| 2003/0235557 A1 | 12/2003 | Gaiger et al. |
| 2010/0015113 A1 | 1/2010 | Restifo et al. |
| 2010/0189742 A1 | 7/2010 | Van Der Burg et al. |
| 2012/0244133 A1 | 9/2012 | Rosenberg et al. |

FOREIGN PATENT DOCUMENTS

| | | |
|---|---|---|
| CN | 1671733 A | 9/2005 |
| CN | 103124740 A | 5/2013 |
| EP | 0239400 B1 | 8/1994 |
| GB | 2188638 A | 10/1987 |

(Continued)

OTHER PUBLICATIONS

Scholten et al. Preservation and redirection of HPV16E7-specific T cell receptors for immunotherapy of cervical cancer. Clinical Immunology 114 (2005) 119-129.*

Choi et al., "Synthesis and Assembly of a Cholera Toxin B Subunit-Rotavirus VP7 Fusion Protein in Transgenic Potato," *Mol. Biotechnol.*, 31: 193-202 (2005).

Dudley et al., "Generation of Tumor-Infiltrating Lymphocyte Cultures for Use in Adoptive Transfer Therapy for Melanoma Patients," *J. Immunother.*, 26(4): 332-342 (2003).

Evans et al., "Antigen Processing Defects in Cervical Carcinomas Limit the Presentation of a CTL Epitope from Human Papillomavirus 16 E6," *J. Immunol.*, 167: 5420-5428 (2001).

(Continued)

*Primary Examiner* — Nianxiang Zou
(74) *Attorney, Agent, or Firm* — Leydig, Voit & Mayer

(57) ABSTRACT

Disclosed is a T cell receptor (TCR) having antigenic specificity for an HLA-A2-restricted epitope of human papillomavirus (HPV) 16 E6, $E6_{29-38}$. Related polypeptides and proteins, as well as related nucleic acids, recombinant expression vectors, host cells, and populations of cells are also provided. Antibodies, or an antigen binding portion thereof, and pharmaceutical compositions relating to the TCRs of the invention are also provided. Also disclosed are methods of detecting the presence of a condition in a mammal and methods of treating or preventing a condition in a mammal, wherein the condition is cancer, HPV 16 infection, or HPV-positive premalignancy.

19 Claims, 6 Drawing Sheets

Specification includes a Sequence Listing.

(56) References Cited

FOREIGN PATENT DOCUMENTS

| JP | H10-509948 A | 9/1998 |
|---|---|---|
| JP | 2013-505734 A | 2/2013 |
| WO | WO 96/15153 A1 | 5/1996 |
| WO | WO 2007/131092 A2 | 11/2007 |
| WO | WO 2011/039508 A2 | 4/2011 |

OTHER PUBLICATIONS

Haskard et al., "The Production of Human Monoclonal Autoantibodies from Patients with Rheumatoid Arthritis by the EBV-Hybridoma Technique," *J. Immunol. Methods*, 74(2): 361-367 (1984).
Hudecz, F., "Synthesis of Peptide Bioconjugates," *Methods Mol. Biol.*, 298: 209-223 (2005).
Huse et al., "Generation of a Large Combinatorial Library of the Immunoglobulin Repertoire in Phage Lambda," *Science*, 246: 1275-1281 (1989).
International Bureau, International Search Report in International Application No. PCT/US2014/046480, mailed Oct. 28, 2014.
International Bureau, Written Opinion in International Application No. PCT/US2014/046480, mailed Oct. 28, 2014.
Kirin et al., "Amino Acid and Peptide Bioconjugates of Copper (II) and Zinc (II) Complexes with a Modified N,N-Bis(2-picolyl)amine Ligand," *Inorg. Chem.*, 44(15): 5405-5415 (2005).
Köhler et al., "Derivation of specific antibody-producing tissue culture and tumor lines by cell fusion," *Eur. J. Immunol.*, 5: 511-519 (1976).
Lyons, G., "Immunotherapeutic strategies against human papillomavirus induced cervical cancer," A Dissertation Submitted to the Faculty of the Graduate School in Candidacy for the Degree of Doctor of Philosophy, Program in Molecular Biology, Chicago, IL (2004).

Murphy et al., "T-cell receptors concentrate diversity in the third hypervariable region," *Janeway's Immunobiology*, 7th Edition, p. 157-158 (2008).
Pedersen et al., "Comparison of surface accessible residues in human and murine immunoglobulin Fv domains. Implication for humanization of murine antibodies," *J. Mol. Biol.*, 235: 959-973 (1994).
Reiter et al., "Engineering interchain disulfide bonds into conserved framework regions of Fv fragments: improved biochemical characteristics of recombinant immunotoxins containing disulfide-stabilized Fv," *Protein Engineering*, 7: 697-704 (1994).
Riddell et al., "The use of anti-CD3 and anti-CD28 monoclonal antibodies to clone and expand human antigen-specific T-cells," *J. Immunol. Methods*, 128: 189-201 (1990).
Roder et al., "The EBV-Hybridoma Techique," *Methods Enzymol.*, 121: 140-167 (1986).
Scholten et al., "Preservation and redirection of HPV16E7-specific T cell receptors for immunotherapy of cervical cancer," *Clin. Immunol.*, 114: 119-129 (2005).
Scholten et al., "Promiscuous behavior of HPV16E6 specific T cell receptor beta chains hampers functional expression in TCR transgenic T cells, which can be restored in part by genetic modification," *Cell Oncol.*, 32: 43-56 (2010).
Scholten et al., "Generating HPV specific T helper cells for the treatment of HPV induced malignancies using TCR gene transfer," *J. Translation. Med.*, 9: 147 (2011).
Thomas et al., "HPV16 E6$_{29\text{-}38}$-specific T cells kill cervical carcinoma cells despite partial evasion of T-cell effector function," *Int. J. Cancer*, 122: 2791-2799 (2008).
Wadhwa et al., "Receptor Mediated Glycotargeting," *J. Drug Targeting*, 3: 111 (1995).

\* cited by examiner

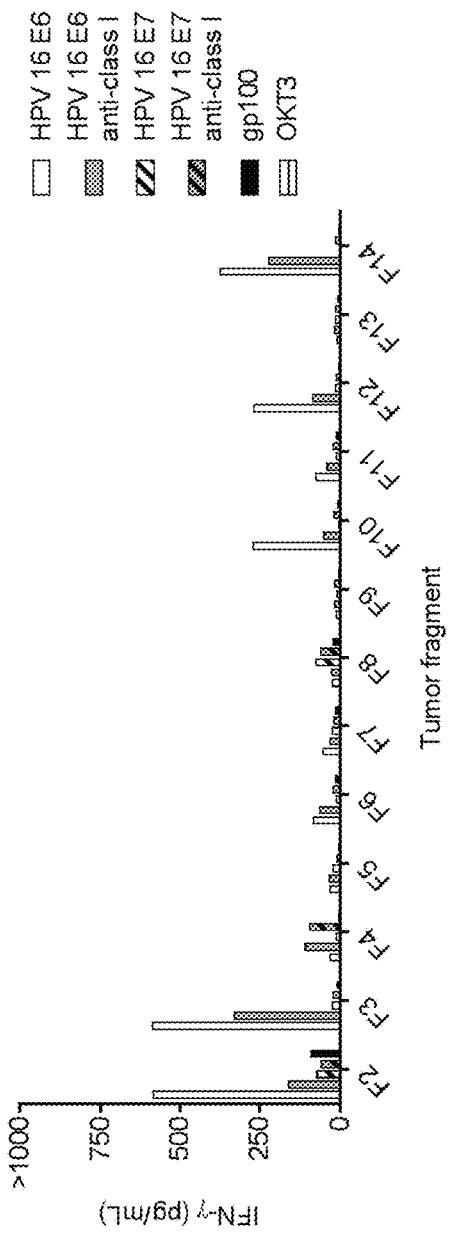
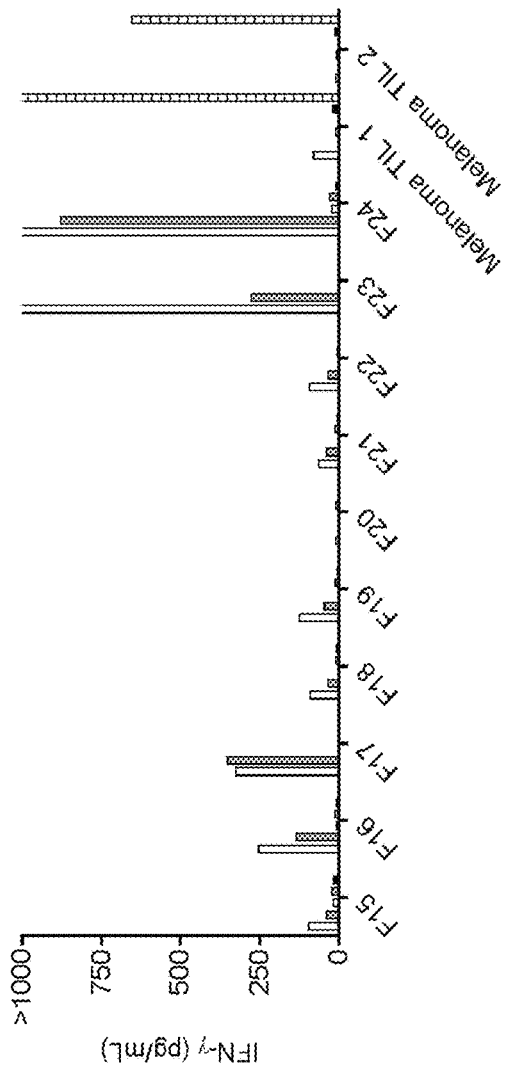
FIG. 2A
FIG. 2B

SEQUENCE LISTING

```
Sequence total quantity: 39
SEQ ID NO: 1              moltype = AA  length = 158
FEATURE                   Location/Qualifiers
REGION                    1..158
                          note = Synthetic
source                    1..158
                          mol_type = protein
                          organism = synthetic construct
SEQUENCE: 1
MHQKRTAMFQ DPQERPRKLP QLCTELQTTI HDIILECVYC KQQLLRREVY DFAFRDLCIV    60
YRDGNPYAVC DKCLKFYSKI SEYRHYCYSL YGTTLEQQYN KPLCDLLIRC INCQKPLCPE   120
EKQRHLDKKQ RFHNIRGRWT GRCMSCCRSS RTRRETQL                           158

SEQ ID NO: 2              moltype = AA  length = 10
FEATURE                   Location/Qualifiers
REGION                    1..10
                          note = Synthetic
source                    1..10
                          mol_type = protein
                          organism = synthetic construct
SEQUENCE: 2
TIHDIILECV                                                           10

SEQ ID NO: 3              moltype = AA  length = 5
FEATURE                   Location/Qualifiers
REGION                    1..5
                          note = Synthetic
source                    1..5
                          mol_type = protein
                          organism = synthetic construct
SEQUENCE: 3
SIFNT                                                                 5

SEQ ID NO: 4              moltype = AA  length = 7
FEATURE                   Location/Qualifiers
REGION                    1..7
                          note = Synthetic
source                    1..7
                          mol_type = protein
                          organism = synthetic construct
SEQUENCE: 4
LYKAGEL                                                               7

SEQ ID NO: 5              moltype = AA  length = 13
FEATURE                   Location/Qualifiers
REGION                    1..13
                          note = Synthetic
source                    1..13
                          mol_type = protein
                          organism = synthetic construct
SEQUENCE: 5
AGHPSSNSGY ALN                                                       13

SEQ ID NO: 6              moltype = AA  length = 5
FEATURE                   Location/Qualifiers
REGION                    1..5
                          note = Synthetic
source                    1..5
                          mol_type = protein
                          organism = synthetic construct
SEQUENCE: 6
SGHVS                                                                 5

SEQ ID NO: 7              moltype = AA  length = 6
FEATURE                   Location/Qualifiers
REGION                    1..6
                          note = Synthetic
source                    1..6
                          mol_type = protein
                          organism = synthetic construct
SEQUENCE: 7
FNYEAQ                                                                6

SEQ ID NO: 8              moltype = AA  length = 14
FEATURE                   Location/Qualifiers
REGION                    1..14
                          note = Synthetic
source                    1..14
```

```
                        mol_type = protein
                        organism = synthetic construct
SEQUENCE: 8
ASSSQTGART DTQY                                                         14

SEQ ID NO: 9            moltype = AA   length = 131
FEATURE                 Location/Qualifiers
REGION                  1..131
                        note = Synthetic
source                  1..131
                        mol_type = protein
                        organism = synthetic construct
SEQUENCE: 9
MLLEHLLIIL WMQLTWVSGQ QLNQSPQSMF IQEGEDVSMN CTSSSIFNTW LWYKQDPGEG        60
PVLLIALYKA GELTSNGRLT AQFGITRKDS FLNISASIPS DVGIYFCAGH PSSNSGYALN       120
FGKGTSLLVT P                                                           131

SEQ ID NO: 10           moltype = AA   length = 135
FEATURE                 Location/Qualifiers
REGION                  1..135
                        note = Synthetic
source                  1..135
                        mol_type = protein
                        organism = synthetic construct
SEQUENCE: 10
MGTSLLCWVV LGFLGTDHTG AGVSQSPRYK VTKRGQDVAL RCDPISGHVS LYWYRQALGQ        60
GPEFLTYFNY EAQQDKSGLP NDRFSAERPE GSISTLTIQR TEQRDSAMYR CASSSQTGAR       120
TDTQYFGPGT RLTVL                                                       135

SEQ ID NO: 11           moltype = AA   length = 272
FEATURE                 Location/Qualifiers
REGION                  1..272
                        note = Synthetic
source                  1..272
                        mol_type = protein
                        organism = synthetic construct
SEQUENCE: 11
MLLEHLLIIL WMQLTWVSGQ QLNQSPQSMF IQEGEDVSMN CTSSSIFNTW LWYKQDPGEG        60
PVLLIALYKA GELTSNGRLT AQFGITRKDS FLNISASIPS DVGIYFCAGH PSSNSGYALN       120
FGKGTSLLVT PHIQNPDPAV YQLRDSKSSD KSVCLFTDFD SQTNVSQSKD SDVYITDKTV       180
LDMRSMDFKS NSAVAWSNKS DFACANAFNN SIIPEDTFFP SPESSCDVKL VEKSFETDTN       240
LNFQNLSVIG FRILLLKVAG FNLLMTLRLW SS                                    272

SEQ ID NO: 12           moltype = AA   length = 314
FEATURE                 Location/Qualifiers
REGION                  1..314
                        note = Synthetic
source                  1..314
                        mol_type = protein
                        organism = synthetic construct
SEQUENCE: 12
MGTSLLCWVV LGFLGTDHTG AGVSQSPRYK VTKRGQDVAL RCDPISGHVS LYWYRQALGQ        60
GPEFLTYFNY EAQQDKSGLP NDRFSAERPE GSISTLTIQR TEQRDSAMYR CASSSQTGAR       120
TDTQYFGPGT RLTVLEDLKN VFPPEVAVFE PSEAEISHTQ KATLVCLATG FYPDHVELSW       180
WVNGKEVHSG VSTDPQPLKE QPALNDSRYC LSSRLRVSAT FWQNPRNHFR CQVQFYGLSE       240
NDEWTQDRAK PVTQIVSAEA WGRADCGFTS ESYQQGVLSA TILYEILLGK ATLYAVLVSA       300
LVLMAMVKRK DSRG                                                        314

SEQ ID NO: 13           moltype = AA   length = 141
FEATURE                 Location/Qualifiers
REGION                  1..141
                        note = Synthetic
source                  1..141
                        mol_type = protein
                        organism = synthetic construct
SEQUENCE: 13
HIQNPDPAVY QLRDSKSSDK SVCLFTDFDS QTNVSQSKDS DVYITDKTVL DMRSMDFKSN        60
SAVAWSNKSD FACANAFNNS IIPEDTFFPS PESSCDVKLV EKSFETDTNL NFQNLSVIGF       120
RILLLKVAGF NLLMTLRLWS S                                                141

SEQ ID NO: 14           moltype = AA   length = 179
FEATURE                 Location/Qualifiers
REGION                  1..179
                        note = Synthetic
source                  1..179
                        mol_type = protein
                        organism = synthetic construct
SEQUENCE: 14
EDLKNVFPPE VAVFEPSEAE ISHTQKATLV CLATGFYPDH VELSWWVNGK EVHSGVSTDP        60
```

```
QPLKEQPALN DSRYCLSSRL RVSATFWQNP RNHFRCQVQF YGLSENDEWT QDRAKPVTQI    120
VSAEAWGRAD CGFTSESYQQ GVLSATILYE ILLGKATLYA VLVSALVLMA MVKRKDSRG    179

SEQ ID NO: 15           moltype = AA  length = 137
FEATURE                 Location/Qualifiers
REGION                  1..137
                        note = Synthetic
source                  1..137
                        mol_type = protein
                        organism = synthetic construct
SEQUENCE: 15
DIQNPEPAVY QLKDPRSQDS TLCLFTDFDS QINVPKTMES GTFITDKTVL DMKAMDSKSN    60
GAIAWSNQTS FTCQDIFKET NATYPSSDVP CDATLTEKSF ETDMNLNFQN LSVMGLRILL   120
LKVAGFNLLM TLRLWSS                                                  137

SEQ ID NO: 16           moltype = AA  length = 173
FEATURE                 Location/Qualifiers
REGION                  1..173
                        note = Synthetic
source                  1..173
                        mol_type = protein
                        organism = synthetic construct
SEQUENCE: 16
EDLRNVTPPK VSLFEPSKAE IANKQKATLV CLARGFFPDH VELSWWVNGK EVHSGVSTDP    60
QAYKESNYSY CLSSRLRVSA TFWHNPRNHF RCQVQFHGLS EEDKWPEGSP KPVTQNISAE   120
AWGRADCGIT SASYQQGVLS ATILYEILLG KATLYAVLVS TLVVMAMVKR KNS          173

SEQ ID NO: 17           moltype = AA  length = 268
FEATURE                 Location/Qualifiers
REGION                  1..268
                        note = Synthetic
source                  1..268
                        mol_type = protein
                        organism = synthetic construct
SEQUENCE: 17
MLLEHLLIIL WMQLTWVSGQ QLNQSPQSMF IQEGEDVSMN CTSSSIFNTW LWYKQDPGEG    60
PVLLIALYKA GELTSNGRLT AQFGITRKDS FLNISASIPS DVGIYFCAGH PSSNSGYALN   120
FGKGTSLLVT PDIQNPEPAV YQLKDPRSQD STLCLFTDFD SQINVPKTME SGTFITDKTV   180
LDMKAMDSKS NGAIAWSNQT SFTCQDIFKE TNATYPSSDV PCDATLTEKS FETDMNLNFQ   240
NLSVMGLRIL LLKVAGFNLL MTLRLWSS                                      268

SEQ ID NO: 18           moltype = AA  length = 308
FEATURE                 Location/Qualifiers
REGION                  1..308
                        note = Synthetic
source                  1..308
                        mol_type = protein
                        organism = synthetic construct
SEQUENCE: 18
MGTSLLCWVV LGFLGTDHTG AGVSQSPRYK VTKRGQDVAL RCDPISGHVS LYWYRQALGQ    60
GPEFLTYFNY EAQQDKSGLP NDRFSAERPE GSISTLTIQR TEQRDSAMYR CASSSQTGAR   120
TDTQYFGPGT RLTVLEDLRN VTPPKVSLFE PSKAEIANKQ KATLVCLARG FFPDHVELSW   180
WVNGKEVHSG VSTDPQAYKE SNYSYCLSSR LRVSATFWHN PRNHFRCQVQ FHGLSEEDKW   240
PEGSPKPVTQ NISAEAWGRA DCGITSASYQ QGVLSATILY EILLGKATLY AVLVSTLVVM   300
AMVKRKNS                                                            308

SEQ ID NO: 19           moltype = DNA  length = 393
FEATURE                 Location/Qualifiers
misc_feature            1..393
                        note = Synthetic
source                  1..393
                        mol_type = other DNA
                        organism = synthetic construct
SEQUENCE: 19
atgctccttg aacatttatt aataatcttg tggatgcagc tgacatgggt cagtggtcaa    60
cagctgaatc agagtcctca atctatgttt atccaggaag agaagatgt ctccatgaac    120
tgcacttctt caagcatatt taacacctgg ctatggtaca agcaggaccc tggggaaggt   180
cctgtcctct tgatagcctt atataaggct ggtgaattga cctcaaatgg aagactgact   240
gctcagtttg gtataaccag aaaggacagc ttcctgaata tctcagcatc catacctagt   300
gatgtaggca tctacttctg tgctgggcac ccttcctcaa attccgggta tgcactcaac   360
ttcggcaaag gcacctcgct gttggtcaca ccc                                393

SEQ ID NO: 20           moltype = DNA  length = 405
FEATURE                 Location/Qualifiers
misc_feature            1..405
                        note = Synthetic
source                  1..405
                        mol_type = other DNA
                        organism = synthetic construct
```

```
SEQUENCE: 20
atgggcacca gtctcctatg ctgggtggtc ctgggtttcc tagggacaga tcacacaggt    60
gctggagtct cccagtctcc caggtacaaa gtcacaaaga ggggacagga tgtagctctc   120
aggtgtgatc caatttcggg tcatgtatcc ctttattggt accgacaggc cctggggcag   180
ggcccagagt ttctgactta cttcaattat gaagcccaac aagacaaatc agggctgccc   240
aatgatcggt tctctgcaga gaggcctgag ggatccatct ccactctgac gatccagcgc   300
acagagcagc gggactcggc catgtatcgc tgtgccagca gctcccagac aggggcccgc   360
acagatacgc agtattttgg cccaggcacc cggctgacag tgctc                   405

SEQ ID NO: 21           moltype = DNA   length = 819
FEATURE                 Location/Qualifiers
misc_feature            1..819
                        note = Synthetic
source                  1..819
                        mol_type = other DNA
                        organism = synthetic construct
SEQUENCE: 21
atgctccttg aacatttatt aataatcttg tggatgcagc tgacatgggg cagtggtcaa    60
cagctgaatc agagtcctca atctatgttt atccaggaag gagaagatgt ctccatgaac   120
tgcacttctt caagcatatt taacacctgg ctatggtaca agcaggaccc tgggaaggt    180
cctgtcctct tgatagcctt atataaggct ggtgaattga cctcaaatgg aagactgact   240
gctcagtttg gtataaccag aaaggacagc ttcctgaata tctcagcatc cataccagt    300
gatgtaggca tctacttctg tgctgggcac ccttcctcaa attccgggta tgcactcaac   360
ttcggcaaag gcacctcgct gttggtcaca ccccatatcc agaaccctga ccctgccgtg   420
taccagctga gagactctaa atccagtgac aagtctgtct gccattcac cgattttgat   480
tctcaaacaa atgtgtcaca aagtaaggat tctgatgtgt atatcacaga caaaactgtt   540
ctagacatga ggtctatgga cttcaagagc aacagtgctg tggcctggag caacaaatct   600
gactttgcat gtgcaaacgc cttcaacaac agcattattc cagaagacac cttcttcccc   660
agcccagaaa gttcctgtga tgtcaagctg gtcgagaaaa gctttgaaac agatacgaac   720
ctaaactttc aaaacctgtc agtgattggg ttccgaatcc tcctcctgaa agtggccggg   780
tttaatctgc tcatgacgct gcggctgtgg tccagctga                          819

SEQ ID NO: 22           moltype = DNA   length = 945
FEATURE                 Location/Qualifiers
misc_feature            1..945
                        note = Synthetic
source                  1..945
                        mol_type = other DNA
                        organism = synthetic construct
SEQUENCE: 22
atgggcacca gtctcctatg ctgggtggtc ctgggtttcc tagggacaga tcacacaggt    60
gctggagtct cccagtctcc caggtacaaa gtcacaaaga ggggacagga tgtagctctc   120
aggtgtgatc caatttcggg tcatgtatcc ctttattggt accgacaggc cctggggcag   180
ggcccagagt ttctgactta cttcaattat gaagcccaac aagacaaatc agggctgccc   240
aatgatcggt tctctgcaga gaggcctgag ggatccatct ccactctgac gatccagcgc   300
acagagcagc gggactcggc catgtatcgc tgtgccagca gctcccagac aggggcccgc   360
acagatacgc agtattttgg cccaggcacc cggctgacag tgctcgagga cctgaaaaac   420
gtgttcccac ccgaggtcgc tgtgtttgag ccatcagaag cagagatctc ccacaccca   480
aaggccacac tggtgtgcct ggccacaggc ttctacccg accacgtgga gctgagctgg   540
tgggtgaatg ggaaggaggt gcacagtggg gtcagcacag acccgcagcc cctcaaggag   600
cagcccgccc tcaatgactc cagatactgc ctgagcagcc gcctgagggt ctcggccagc   660
ttctggcaga acccccgcaa ccacttccgc tgtcaagtcc agttctacgg gctctcggag   720
aatgacgagt ggacccagga tagggccaaa cctgtcaccc agatcgtcag cgccgaggcc   780
tggggtagag cagactgtgg cttcacctcc gagtcttacc agcaaggggg cctgtctgcc   840
accatcctct atgagatctt gctagggaag gccacccttgt atgccgtgct ggtcagtgcc   900
ctcgtgctga tggccatggt caagagaaag gattccagag gctag                   945

SEQ ID NO: 23           moltype = DNA   length = 426
FEATURE                 Location/Qualifiers
misc_feature            1..426
                        note = Synthetic
source                  1..426
                        mol_type = other DNA
                        organism = synthetic construct
SEQUENCE: 23
catatccaga accctgaccc tgccgtgtac cagctgagag actctaaatc cagtgacaag    60
tctgtctgcc tattcaccga ttttgattct caaacaaatg tgtcacaaag taaggattct   120
gatgtgtata tcacagacaa aactgtgcta gacatgaggt ctatggactt caagagcaac   180
agtgctgtgg cctggagcaa caaatctgac tttgcatgtg caaacgcctt caacaacagc   240
attattccag aagacacctt cttccccagc ccagaaagtt cctgtgatgt caagctggtc   300
gagaaaagct ttgaaacaga tacgaaccta aactttcaaa acctgtcagt gattgggttc   360
cgaatcctcc tcctgaaagt ggccgggttt aatctgctca tgacgctgcg gctgtggtcc   420
agctga                                                              426

SEQ ID NO: 24           moltype = DNA   length = 540
FEATURE                 Location/Qualifiers
misc_feature            1..540
                        note = Synthetic
source                  1..540
```

```
                        mol_type = other DNA
                        organism = synthetic construct
SEQUENCE: 24
gaggacctga aaaacgtgtt cccacccgag gtcgctgtgt ttgagccatc agaagcagag    60
atctcccaca cccaaaaggc cacactggtg tgcctggcca caggcttcta ccccgaccac   120
gtggagctga gctggtgggt gaatgggaag gaggtgcaca gtggggtcag cacagacccg   180
cagcccctca aggagcagcc cgccctcaat gactccagat actgcctgag cagccgcctg   240
agggtctcgg ccaccttctg gcagaacccc cgcaaccact tccgctgtca agtccagttc   300
tacgggctct cggagaatga cgagtggacc caggataggg ccaaacctgt caccagatc    360
gtcagcgccg aggcctgggg tagagcagac tgtggcttca cctccgagtc ttaccagcaa   420
ggggtcctgt ctgccaccat cctctatgag atcttgctag ggaaggccac cttgtatgcc   480
gtgctggtca gtgccctcgt gctgatggcc atggtcaaga gaaaggattc agaggctag    540

SEQ ID NO: 25           moltype = DNA  length = 414
FEATURE                 Location/Qualifiers
misc_feature            1..414
                        note = Synthetic
source                  1..414
                        mol_type = other DNA
                        organism = synthetic construct
SEQUENCE: 25
gacatccaga acccagaacc tgctgtgtac cagttaaaag atcctcggtc tcaggacagc    60
accctctgcc tgttcaccga ctttgactcc caaatcaatg tgccgaaaac catggaatct   120
ggaacgttca tcactgacaa aactgtgctg acatgaaag ctatggattc caagagcaat    180
ggggccattg cctggagcaa ccagacaagc ttcacctgcc aagatatctt caaagagacc   240
aacgccacct accccagttc agacgttccc tgtgatgcca cgttgactga gaaaagcttt   300
gaaacagata tgaacctaaa cttttcaaaac ctgtcagtta tgggactccg aatcctcctg   360
ctgaaagtag ccggatttaa cctgctcatg acgctgaggc tgtggtccag ttga          414

SEQ ID NO: 26           moltype = DNA  length = 522
FEATURE                 Location/Qualifiers
misc_feature            1..522
                        note = Synthetic
source                  1..522
                        mol_type = other DNA
                        organism = synthetic construct
SEQUENCE: 26
gaggatctga gaaatgtgac tccacccaag gtctccttgt ttgagccatc aaaagcagag    60
attgcaaaca aacaaaaggc taccctcgtg tgcttggcca ggggcttctt ccctgaccac   120
gtggagctga gctggtgggt gaatggcaag gaggtccaca gtggggtcag cacgaccct    180
caggcctaca aggagagcaa ttatagctac tgcctgagca gccgcctgag ggtctctgct   240
accttctggc acaatcctcg caaccacttc cgctgccaag tgcagttcca tgggcttca    300
gaggaggaca agtggccaga gggctcaccc aaaacctgtca cacagaacat cagtgcagag   360
gcctggggcc gagcagactg tgggattacc tcagcatcct atcaacaagg ggtcttgtct   420
gccaccatcc tctatgagat cctgctaggg aaagccaccc tgtatgctgt gcttgtcagt   480
acactggtgg tgatggctat ggtcaaaaga aagaattcat ga                      522

SEQ ID NO: 27           moltype = DNA  length = 807
FEATURE                 Location/Qualifiers
misc_feature            1..807
                        note = Synthetic
source                  1..807
                        mol_type = other DNA
                        organism = synthetic construct
SEQUENCE: 27
atgctccttg aacatttatt aataatcttg tggatgcagc tgacatgggt cagtggtcaa    60
cagctgaatc agagtcctca atctatgttt atccaggaag gagaagatgt ctccatgaac   120
tgcacttctt caagcatatt taacccctgg ctatggtaca agcaggaccc tgggaaggt    180
cctgtcctct tgatagcctt atataaggct ggtgaattga cctcaaatgg aagactgact   240
gctcagtttg gtataaccag aaaggacagc ttcctgaata tctcagcatc catacctagt   300
gatgtaggca tctacttctg tgctgggcac ccttcctcaa attccgggta tgcactcaac   360
ttcggcaaag gcacctcgct gttggtcaca cccgacatcc agaacccaga acctgctgtg   420
taccagttaa agatcctcgg tctcaggac agcaccctct gcctgttcac cgactttgac   480
tcccaaatca atgtgccgaa aaccatgaa tctggaactt catcactgac caaaactgtg   540
ctggacatga agctatggaa ttccaagagc aatgggccca ttgcctggag caaccagaca   600
agcttcacct gccagatat cttcaaagag accaacgcca cctacccag ttcagacgtt    660
ccctgtgatg ccacgttgac tgagaaaagc tttgaaacag atatgaacct aaactttcaa   720
aacctgtcag ttatgggact ccgaatcctc ctgctgaaag tagccggatt taacctgctc   780
atgacgctga ggctgtggtc cagttga                                      807

SEQ ID NO: 28           moltype = DNA  length = 927
FEATURE                 Location/Qualifiers
misc_feature            1..927
                        note = Synthetic
source                  1..927
                        mol_type = other DNA
                        organism = synthetic construct
SEQUENCE: 28
atgggcacca gtctcctatg ctgggtggtc ctgggttttc tagggacaga tcacacaggt    60
```

```
gctggagtct cccagtctcc caggtacaaa gtcacaaaga ggggacagga tgtagctctc    120
aggtgtgatc caatttcggg tcatgtatcc ctttattggt accgacaggc cctggggcag    180
ggcccagagt ttctgactta cttcaattat gaagcccaac aagacaaatc agggctgccc    240
aatgatcggt tctctgcaga gaggcctgag ggatccatct ccactctgac gatccagcgc    300
acagagcagg gggactcggc catgtatcgc tgtgccagca gctcccagac aggggcccgc    360
acagatacgc agtattttgg cccaggcacc cggctgacag tgctcgagga tctgagaaat    420
gtgactccac ccaaggtctc cttgtttgag ccatcaaaag cagagattgc aaacaaacaa    480
aaggctaccc tcgtgtgctt ggccaggggc ttcttccctg accacgtgga gctgagctgg    540
tgggtgaatg gcaaggaggt ccacagtggg gtcagcacgg accctcaggc ctacaaggag    600
agcaattata gctactgcct gagcagccgc ctgagggtct ctgctacctt ctggcacaat    660
cctcgcaacc acttccgctg ccaagtgcag ttccatgggc tttcagagga ggacaagtgg    720
ccagagggct cacccaaacc tgtcacacag aacatcagtg cagaggcctg gggccgagca    780
gactgtggaa ttacctcagc atcctatcaa caagggcgtc tgtctgccac catcctctat    840
gagatcctgc tagggaaagc caccctgtat gctgtgcttg tcagtacact ggtggtgatg    900
gctatggtca aagaaagaa ttcatga                                         927

SEQ ID NO: 29           moltype = DNA  length = 1815
FEATURE                 Location/Qualifiers
misc_feature            1..1815
                        note = Synthetic
source                  1..1815
                        mol_type = other DNA
                        organism = synthetic construct
SEQUENCE: 29
atggcccttg aacatctgtt gataatactg tggatgcaac ttacctgggt atctggtcag     60
caattgaacc agtctccaca gtccatgttt atccaagaag ggaggacgt gtccatgaat    120
tgtacaagct ccagtatctt caacacgtgg ctgtggtaca acaggatcc tggggaagga    180
ccagtactgt tgatagccct ctataaggcg ggcgaactga catccaatgg aagactcaca    240
gcccaattcg gaattacccg gaaggattct ttcctcaaca tctccgcgag tattccatct    300
gatgtaggaa tatacttctg tgcagggcat ccgtctagca acagtggata tgccctcaat    360
tttggaaagg gcacctccct gctggttacc ccagacattc agaaccccga accagccgta    420
tatcagttga aggacccaag atctcaggat agtacactct gtttgtttac ggactttgac    480
tcacaaatca acgtcccgaa gactatgaaa gtggtacgt tcatcacaga taagacggtt    540
ctggacatga aggctatgga ctcaaagagc aacggggcaa ttgcttggtc caaccagaa    600
agctttacct gtcaggacat ttttaaggag actaatgcta cttatccctc cagcgacgtt    660
ccgtgtgatg cgactcttac cgagaagtct tttgagaccg atatgaatct caacttccag    720
aatctgtcag tgatgggtct gcggatcctg cttctgaagg ttgcaggatt caatcttctt    780
atgactctcc ggctctggtc ttcaagagcc aaaagaagtg gttctggcgc gacgaatttt    840
agtttgctta agcaagccgg agatgtggag gaaaatcctg gaccgatggg cacaagttg    900
ctgtgctggg ttgtgttggg ctttctgggt acagatcata ctggggcggg agtctctcaa    960
agcccccgat acaaagtcac taaaagagg caggatgtcg cgcttcgctg tgatcccatt   1020
agcgggcatg tctccctta ttggtaccgg caggcttgg gacaaggacc ggagttcctc   1080
acttacttca actacgaagc gcagcaggac aagtccgagc tgcctaatga tagattcagc   1140
gccgagagac cggagggcag tatctctact cttacgatac aaagaacgga gcagcgagac   1200
tctgctatgt atagatgtgc aagttctagc cagacgggtg ctcgcacgga cactcaatat   1260
ttcggtcctg gtacaagatt gaccgtcttg gaggatctcc ggaacgtcac cccaccaag   1320
gtcagtttgt ttgagccatc aaaggcggag atgccaaca aacagaaagc tacgctcgtg   1380
tgtttggctc ggggcttctt cccagaccac gtagaacttt cctggtggt caatggaag   1440
gaggttcatt ccggagtgtc cactgatccc aagcgtaca aggaatcaa ctatagctac   1500
tgtctctcat ctcggctccg ggtgagtgcg acattctggc ataatcctcg gaaccacttt   1560
cgatgccaag tgcagtttca tgggttgagc gaggaagaca agtagcccga gggcagtcct   1620
aaaccagtca ctcaaaacat aagcgccgag gatgggga gagccgattg tgggattact   1680
agcgcttcat accaacaagg ggtattgagc gctacaattc tttacgaaat tctcctcggc   1740
aaggcgacgc tctacgccgt actggtgtct actctcgtgg ttatggcaat ggtgaaacgg   1800
aaaaacagct aatga                                                   1815

SEQ ID NO: 30           moltype = DNA  length = 7325
FEATURE                 Location/Qualifiers
misc_feature            1..7325
                        note = Synthetic
source                  1..7325
                        mol_type = other DNA
                        organism = synthetic construct
SEQUENCE: 30
ccatggccct tgaacatctg ttgataaatac tgtggatgca acttacctgg gtatctggtc     60
agcaattgaa ccagtctcca cagtccatgt ttatccaaga aggggaggac gtgtccatga    120
attgtacaag ctccagtatc ttcaacacgt ggctgtggta caaacaggat cctggggaag    180
gaccagtact gttgatagcc ctctataagg cgggcgaact gacatccaat ggaagactca    240
cagcccaatt cggaattacc cggaaggatt ctttcctcaa catctccgcg agtattccat    300
ctgatgtagg aatatacttc tgtgcagggc atccgtctag caacagtgga tatgccctca    360
attttggaaa gggcacctcc ctgctggtta ccccagacat tcagaacccc gaaccagccg    420
tatatcagtt gaaggaccca agatctcagg atagtacact ctgtttgttt acggactttg    480
actcacaaat caacgtcccg aagactatgg aaagtggtac gttcatcaca gataagacgg    540
ttctggacat gaaggctatg gactcaaaga gcaacggggc aattgcttgg tccaaccaga    600
aagctttac ctgtcaggac attttaagg agactaatgc tacttatccc tccagcgacg    660
ttccgtgtga tgcgactctt accgagaagt cttttgagac cgatatgaat ctcaacttcc    720
agaatcgtc agtgatgggt ctgcggatcc tgcttctgaa ggttgcagga ttcaatcttc    780
ttatgactct ccggctctgg tcttcaagag ccaaaagaag tggttctggc gcgacgaatt    840
ttagtttgct taagcaagcc ggagatgtgg aggaaaatcc tggaccgatg gcacaagtt    900
```

```
tgctgtgctg ggttgtgttg ggctttctgg gtacagatca tactgggcg ggagtctctc      960
aaagccccg atacaaagtc actaaaagag ggcaggatgt cgcgcttcgc tgtgatccca     1020
ttagcgggca tgtctcccctt tattggtacc ggcaggcttt gggacaagga ccggagttcc    1080
tcacttactt caactacgaa gcgcagcagg acaagtccgg tctgcctaat gatagattca    1140
gcgccgagag accggagggc agtatctcta ctcttacgat acaaagaacg gagcagcgag    1200
actctgctat gtatagatgt gcaagttcta gccagacggg tgctcgcacg gacactcaat    1260
atttcggtcc tggtacaaga ttgaccgtct tggaggatct ccggaacgtc accccaccaa    1320
aggtcagttt gtttgagcca tcaaaggcgg agatcgccaa caaacagaaa gctacgctcg    1380
tgtgtttggc tcggggcttc ttcccagacc acgtagaact ttcctggtgg gtcaatggaa    1440
aggaggttca ttccggagtg tccactgatc cccaagcgta caaggaatcc aactatagct    1500
actgtctctc atctcggctc cgggtgagtg cgacattctg gcataatcct cggaaccact    1560
ttcgatgcca agtgcagttt catgggttga gcgaggaaga caagtgggcc gagggcagtc    1620
ctaaaccagt cactcaaaac ataagcgccg aggcatgggg tagagccgat tgtgggatta    1680
ctagcgcttc ataccaacaa ggggtattga gcgctacaat tctttacgaa attctcctcg    1740
gcaaggcgac gctctacgcc gtactggtgt ctactctcgt ggttatggca atggtgaaac    1800
ggaaaaacag ctaatgagaa ttctgcagtc gacggtaccg cgggcccggg atccgataaa    1860
ataaaagatt ttatttagtc tccagaaaaa ggggggaatg aaagacccca cctgtaggtt    1920
tggcaagcta gcttaagtaa cgccatttg caaggcatgg aaaatacata actgagaata    1980
gagaagttca gatcaaggtt aggaacagag agacagcaga atatgggcca aacaggatat    2040
ctgtggtaag cagttcctgc cccggctcag ggccaagaac agatggtccc cagatgcggt    2100
cccgcctca gcagtttcta gagaaccatc agatgtttcc agggtgcccc aaggacctga    2160
aaatgaccct gtgccttatt tgaactaacc aatcagttcg cttctcgctt ctgttcgcgc    2220
gcttctgctc cccgagctca ataaaagagc ccaaccccc tcactcggcg cgccagtcct    2280
ccgatagact gcgtcgcccg ggtacccgtg tatccaataa accctcttgc agttgcatcc    2340
gacttgtggt ctcgctgttc cttggagggt tctcctctga gtgattgact acccgtcagc    2400
ggggtctttt catgggtaac agtttcttga agttggagaa caacattctg agggtaggag    2460
tcgaatatta agtaatcctg actcaattag ccactgtttt gaatccacat actccaatac    2520
tcctgaaatc catcgatgga gttcattatg gacagcgcag aaaagctgg ggagaattgt    2580
gaaattgtta tccgctcaca attccacaca acatacgagc cggaagcata aagtgtaaag    2640
cctggggtgc ctaatgagtg agctaactca cattaattgc gttgcgctca ctgcccgctt    2700
tccagtcggg aaacctgtcg tgccagctgc attaatgaat cggccaacgc gcggggagag    2760
gcggtttgcg tattgggcgc tcttccgctt cctcgctcac tgactcgctg cgctcggtcg    2820
ttcggctgcg cgagcggta tcagctcact caaaggcggt aatacggtta ccacagaat    2880
cagggggataa cgcaggaaag aacatgtgag caaaaggcca gcaaaaggcc aggaaccgta    2940
aaaaggccgc gttgctggcg tttttccata ggctccgccc ccctgacgag catcacaaaa    3000
atcgacgctc aagtcagagg tggcgaaacc cgacaggact ataaagatac caggcgtttc    3060
cccctggaag ctccctcgtg cgctctcctg ttccgaccct gccgcttacc ggatacctgt    3120
ccgcctttct cccttcggga agcgtggcgc tttctcatag ctcacgctgt aggtatctca    3180
gttcggtgta ggtcgttcgc tccaagctgg gctgtgtgca cgaaccccc gttcagccccg    3240
accgctgcgc cttatccggt aactatcgtc ttgagtccaa cccggtaaga cacgacttat    3300
cgccactggc agcagccact ggtaacagga ttagcagagc gaggtatgta ggcggtgcta    3360
cagagttctt gaagtggtgg cctaactacg gctacactag aagaacagta tttggtatct    3420
gcgctctgct gaagccagtt accttcggaa aaagagttgg tagctcttga tccggcaaac    3480
aaaccaccgc tggtagcggt ggtttttttg tttgcaagca gcagattacg cgcagaaaaa    3540
aaggatctca agaagatcct ttgatctttt ctacggggtc tgacgctcag tggaacgaaa    3600
actcacgtta agggattttg gtcatgagat tatcaaaaag gatcttcacc tagatccttt    3660
taaattaaaa atgaagtttt aaatcaatct aaagtatata tgagtaaact tggtctgaca    3720
gttaccaatg cttaatcagt gaggcaccta tctcagcgat ctgtctattt cgttcatcca    3780
tagttgcctg actccccgtc gtgtagataa ctacgatacg ggagggctta ccatctggcc    3840
ccagtgctgc aatgataccg cgagacccac gctcaccggc tccagattta tcagcaataa    3900
accagccagc cggaagggcc gagcgcagaa gtggtcctgc aactttatcc gcctccatcc    3960
agtctattaa ttgttgccgg gaagctagag taagtagttc gccagttaat agtttgcgca    4020
acgttgttgc cattgctaca ggcatcgtgg tgtcacgctc gtcgtttggt atggcttcat    4080
tcagctccgg ttcccaacga tcaaggcgag ttacatgatc cccatgttg tgcaaaaaag    4140
cggttagctc cttcggtcct ccgatcgttg tcagaagtaa gttggccgca gtgttatcac    4200
tcatggttat ggcagcactg cataattctc ttactgtcat gccatccgta agatgctttt    4260
ctgtgactgg tgagtactca accaagtcat tctgagaata gtgtatgcgg cgaccgagtt    4320
gctcttgccc ggcgtcaata cgggataata ccgcgccaca gcagaact ttaaaagtgc    4380
tcatcattgg aaaacgttct cggggcgaa aactctcaag gatcttaccg ctgttgagat    4440
ccagttcgat gtaacccact cgtgcaccca actgatcttc agcatctttt actttcacca    4500
gcgtttctgg gtgagcaaaa acaggaaggc aaaatgccgc aaaaaaggga taagggcga    4560
cacgaaaatg ttgaatactc atactcttcc tttttcaata ttattgaagc atttatcagg    4620
gttattgtct catgagcgga tacatatttg aatgtattta gaaaaataaa caaataggg    4680
ttccgcgcac atttcccga aaagtgccac ctgacgtcta agaaaccatt attatcatga    4740
cattaaccta taaaaatagg cgtatcacga ggccctttcg tctcgcgcgt ttcggtgatg    4800
acggtgaaaa cctctgacac atgcagctcc cggagacggt cacagcttgt ctgtaagcgg    4860
atgccggag cagacaagcc cgtcagggcg cgtcagcggg tgttggcggg tgtcgggct    4920
ggcttaacta tgcggcatca gagcagattg tactgagagt gcaccatatg cggtgtgaaa    4980
taccgcacag atgcgtaagg agaaaatacc gcatcaggcg ccattcaggc tgcgcaactg    5040
ttgggaaggg cgatcggtgc gggcctcttc gctattacgc cagctggcga aagggggatg    5100
tgctgcaagg cgattaagtt gggtaacgcc agggttttcc cagtcacgac gttgtaaaac    5160
gacggcgcaa ggaatggtgc atgcaaggag atgcgcccaa caaccgctcc atgagcccga    5220
agtggcgagc cgatcttccc catcggtga tgtcggcgat ataggcgcca gcaaccgcac    5280
ctggcgatgcc gccacgatgc gtccggcgta gaggcgatta gtccaatttg tttaagacag    5340
gatatcagtg gtccaggctc tagttttgac tcaacaatat caccagctga agcctataga    5400
gtacgagcca tagataaaat aaagattt atttagtctc cagaaaaagg ggggaatgaa    5460
agaccccacc tgtaggtttg gcaagctagc ttaagtaacg ccattttgca aggcatggaa    5520
aatacataac tgagaataga agcagaattc aagagcagaag aagaagaga acagcagaat    5580
```

-continued

```
atgggccaaa caggatatct gtggtaagca gttcctgccc cggctcaggg ccaagaacag   5700
atggtcccca gatgcggtcc cgccctcagc agtttctaga gaaccatcag atgtttccag   5760
ggtgccccaa ggacctgaaa tgaccctgtg ccttatttga actaaccaat cagttcgctt   5820
ctcgcttctg ttcgcgcgct tctgctcccc gagctcaata aaagagccca caaccccctca   5880
ctcgcgcgcg cagtcctccg atagactgcg tcgcccgggt accgtattc ccaataaagc   5940
ctcttgctgt ttgcatccga atcgtggact cgctgatcct tgggagggtc tcctcagatt   6000
gattgactgc ccacctcggg ggtctttcat ttggaggttc caccgagatt tggagacccc   6060
tgcccaggga ccaccgaccc cccgccgggg aggtaagctg gccagcggtc gtttcgtgtc   6120
tgtctctgtc tttgtgcgtg tttgtgccgg catctaatgt ttgcgcctgc gtctgtacta   6180
gttagctaac tagctctgta tctggcggac ccgtggtgga actgacgagt tcggaacacc   6240
cggccgcaac cctgggagac gtcccaggga cttcgggggc cgttttgtg cccgacctg   6300
agtcctaaaa tcccgatcgt ttaggactct ttggtgcacc cccttagag gagggatatg   6360
tggttctggt aggagacgag aacctaaaac agttcccgcc tccgtctgaa ttttgctt   6420
cggtttggga ccgaagccgc gccgcgcgtc ttgtctgctta cagcatcgtt ctgtgttgtc   6480
tctgtctgac tgtgtttctg tatttgtctg aaaatatggg cccgggctag cctgttacca   6540
ctccctaag tttgaccttaa ggtcactgga aagatgtcga gcggatcgct cacaaccagt   6600
cggtagatgt caagaagaga cgttgggtta ccttctgctc tgcagaatgg ccaaccttta   6660
acgtcggatg gccgcgagac ggcacctttaa accgagaccct catcacccag gttaagatca   6720
aggtctttc acctggcccg catggacacc cagaccaggt ccctacatc gtgacctggg   6780
aagccttggc tttgacccc cctcccgg tcaagccctt tgtacaccct aagcctccgc   6840
ctcctcttcc tccatccgcc ccgtctctcc cccttgaacc tcctgttcg accccgcctc   6900
gatcctccct ttatccagcc ctcactcctt ctctaggcgc tcatatgag   6960
tcttatatgg ggcaccccg ccccttgtaa acttccctga ccctgacatg caagagtta   7020
ctaacagccc ctctctccaa gctcacttac aggctctcta cttagtccag cacgaagtct   7080
ggagacctct ggcggcagcc taccaagaac aactggaccg accgtggta cctcacccctt   7140
accgagtcgg cgacacagtg tgggtccgcc gacaccagac taagaaccta gaacctgcc   7200
ggaaaggacc ttacacagtc ctgctgacca cccccacccgc cctcaaagta gacggcatcg   7260
cagcttggat acacgccgcc cacgtgaagg ctgccgaccc cggggggtgga ccatcctcta   7320
gaccg                                                               7325

SEQ ID NO: 31          moltype = DNA    length = 15
FEATURE                Location/Qualifiers
misc_feature           1..15
                       note = Synthetic
source                 1..15
                       mol_type = other DNA
                       organism = synthetic construct
SEQUENCE: 31
agcatattta acacc                                                    15

SEQ ID NO: 32          moltype = DNA    length = 21
FEATURE                Location/Qualifiers
misc_feature           1..21
                       note = Synthetic
source                 1..21
                       mol_type = other DNA
                       organism = synthetic construct
SEQUENCE: 32
ttatataagg ctggtgaatt g                                             21

SEQ ID NO: 33          moltype = DNA    length = 39
FEATURE                Location/Qualifiers
misc_feature           1..39
                       note = Synthetic
source                 1..39
                       mol_type = other DNA
                       organism = synthetic construct
SEQUENCE: 33
gctgggcacc cttcctcaaa ttccgggtat gcactcaac                          39

SEQ ID NO: 34          moltype = DNA    length = 15
FEATURE                Location/Qualifiers
misc_feature           1..15
                       note = Synthetic
source                 1..15
                       mol_type = other DNA
                       organism = synthetic construct
SEQUENCE: 34
tcgggtcatg tatcc                                                    15

SEQ ID NO: 35          moltype = DNA    length = 18
FEATURE                Location/Qualifiers
misc_feature           1..18
                       note = Synthetic
source                 1..18
                       mol_type = other DNA
                       organism = synthetic construct
SEQUENCE: 35
ttcaattatg aagcccaa                                                 18
```

```
SEQ ID NO: 36          moltype = DNA  length = 42
FEATURE                Location/Qualifiers
misc_feature           1..42
                       note = Synthetic
source                 1..42
                       mol_type = other DNA
                       organism = synthetic construct
SEQUENCE: 36
gccagcagct cccagacagg ggcccgcaca gatacgcagt at                    42

SEQ ID NO: 37          moltype = AA  length = 27
FEATURE                Location/Qualifiers
REGION                 1..27
                       note = Synthetic
source                 1..27
                       mol_type = protein
                       organism = synthetic construct
SEQUENCE: 37
RAKRSGSGAT NFSLLKQAGD VEENPGP                                     27

SEQ ID NO: 38          moltype = DNA  length = 393
FEATURE                Location/Qualifiers
misc_feature           1..393
                       note = Synthetic
source                 1..393
                       mol_type = other DNA
                       organism = synthetic construct
SEQUENCE: 38
atggcccttg aacatctgtt gataatactg tggatgcaac ttacctgggt atctggtcag 60
caattgaacc agtctccaca gtccatgttt atccaagaag gggaggacgt gtccatgaat 120
tgtacaagct ccagtatctt caacacgtgg ctgtggtaca aacaggatcc tggggaagga 180
ccagtactgt tgatagccct ctataaggcg ggcgaactga catccaatgg aagactcaca 240
gcccaattcg gaattacccg gaaggattct ttcctcaaca tctccgcgag tattccatct 300
gatgtaggaa tatacttctg tgcagggcat ccgtctagca acagtggata tgccctcaat 360
tttggaaagg gcacctccct gctggttacc cca                              393

SEQ ID NO: 39          moltype = DNA  length = 405
FEATURE                Location/Qualifiers
misc_feature           1..405
                       note = Synthetic
source                 1..405
                       mol_type = other DNA
                       organism = synthetic construct
SEQUENCE: 39
atgggcacaa gtttgctgtg ctgggttgtg ttgggctttc tgggtacaga tcatactggg 60
gcgggagtct ctcaaagccc ccgatacaaa gtcactaaaa gagggcagga tgtcgcgctt 120
cgctgtgatc ccattagcgg gcatgtctcc ctttattggt accggcaggc tttgggacaa 180
ggaccggagt tcctcactta cttcaactac gaagcgcagc aggacaagtc cggtctgcct 240
aatgatagat tcagcgccga gagaccggag ggcagtatct ctactcttac gatacaaaga 300
acggagcagc gagactctgc tatgtataga tgtgcaagtt ctagccagac gggtgctcgc 360
acggacactc aatatttcgg tcctggtaca agattgaccg tcttg                 405
```

US 12,187,779 B2

ANTI-HUMAN PAPILLOMAVIRUS 16 E6 T CELL RECEPTORS

CROSS-REFERENCE TO RELATED APPLICATIONS

This patent application is a continuation of U.S. application Ser. No. 17/142,486, filed Jan. 6, 2021, which is a continuation of U.S. application Ser. No. 16/408,939, filed May 10, 2019, which issued as U.S. Pat. No. 10,913,785, which is a continuation of U.S. application Ser. No. 15/786,966, filed Oct. 18, 2017, which issued as U.S. Pat. No. 10,329,339, which is a continuation of U.S. application Ser. No. 14/905,108, filed Jan. 14, 2016, which issued as U.S. Pat. No. 9,822,162, which is the U.S. national phase of International Patent Application No. PCT/US2014/046480, filed Jul. 14, 2014, which claims the benefit of U.S. Provisional Patent Application No. 61/846,167, filed Jul. 15, 2013, each of which is incorporated herein by reference in its entirety.

STATEMENT REGARDING FEDERALLY SPONSORED RESEARCH AND DEVELOPMENT

This invention was made with Government support under project numbers ZIABC011477 and BC010984-5 by the National Institutes of Health, National Cancer Institute. The Government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 67,470 Byte XML file named "767470.XML," dated May 24, 2023.

BACKGROUND OF THE INVENTION

The primary cause of some cancer types such as, for example, uterine cervical cancer, is human papillomavirus (HPV) infection. Despite advances in treatments such as chemotherapy, the prognosis for many cancers, including HPV-associated cancers, may be poor. Accordingly, there exists an unmet need for additional treatments for cancer, particularly HPV-associated cancers.

BRIEF SUMMARY OF THE INVENTION

An embodiment of the invention provides a T cell receptor (TCR) having antigenic specificity for human papillomavirus (HPV) 16 E6 and comprising a human variable region and a murine constant region.

Another embodiment of the invention provides an isolated or purified TCR having antigenic specificity for HPV 16 E6 and comprising the amino acid sequences of SEQ ID NOs: 3-8.

The invention further provides related polypeptides and proteins, as well as related nucleic acids, recombinant expression vectors, host cells, and populations of cells. Further provided by the invention are antibodies, or antigen binding portions thereof, and pharmaceutical compositions relating to the TCRs (including functional portions and functional variants thereof) of the invention.

Methods of detecting the presence of a condition in a mammal and methods of treating or preventing a condition in a mammal, wherein the condition is cancer, HPV 16 infection, or HPV-positive premalignancy, are further provided by the invention. The inventive method of detecting the presence of a condition in a mammal comprises (i) contacting a sample comprising cells of the condition with any of the inventive TCRs (including functional portions and functional variants thereof), polypeptides, proteins, nucleic acids, recombinant expression vectors, host cells, populations of host cells, antibodies, or antigen binding portions thereof, or pharmaceutical compositions described herein, thereby forming a complex, and (ii) detecting the complex, wherein detection of the complex is indicative of the presence of the condition in the mammal, wherein the condition is cancer, HPV 16 infection, or HPV-positive premalignancy.

The inventive method of treating or preventing a condition in a mammal comprises administering to the mammal any of the TCRs (including functional portions and functional variants thereof), polypeptides, or proteins described herein, any nucleic acid or recombinant expression vector comprising a nucleotide sequence encoding any of the TCRs (including functional portions and functional variants thereof), polypeptides, proteins described herein, or any host cell or population of host cells comprising a recombinant vector which encodes any of the TCRs (including functional portions and functional variants thereof), polypeptides, or proteins described herein, in an amount effective to treat or prevent the condition in the mammal, wherein the condition is cancer, HPV 16 infection, or HPV-positive premalignancy.

BRIEF DESCRIPTION OF THE SEVERAL VIEWS OF THE DRAWINGS

FIGS. 2A and 2B are bar graphs showing interferon-gamma (IFN-γ) (pg/mL) secreted by tumor infiltrating lymphocytes (TIL) from fragments (F) 2-14 of tumor 3809 (A), fragments 15-24 (B) of tumor 3809, or melanoma TIL upon co-culture with autologous dendritic cells (DCs) which had been pulsed with HPV 16 E6 alone (white bars), HPV 16 E6 in combination with anti-class I antibody (shaded unhatched bars), HPV 16 E7 alone (unshaded hatched bars), HPV 16 E7 in combination with anti-class I antibody (shaded hatched bars), gp100 (black bars), or OKT3 (horizontal striped bars).

DETAILED DESCRIPTION OF THE INVENTION

Figure 1:
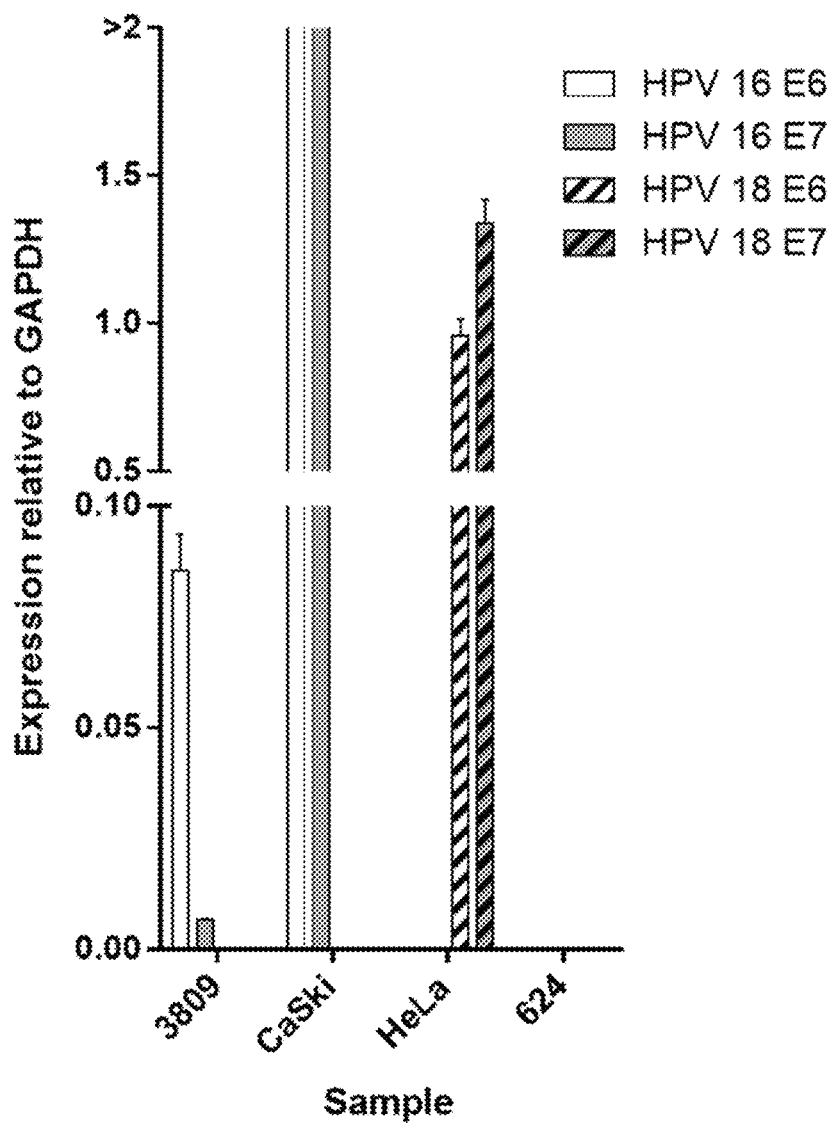
FIG. 1 is a bar graph showing expression of HPV 16 E6 (white bars), HPV 16 E7 (shaded unhatched bars), HPV 18 E6 (unshaded hatched bars), or HPV 18 E7 (shaded hatched bars) relative to glyceraldehyde 3-phosphate dehydrogenase (GAPDH) expression by CaSki cells, HeLa cells, 624 cells, or cells from tumor 3809.

An embodiment of the invention provides a T cell receptor (TCR), and functional portions and functional variants thereof, having antigenic specificity for human papillomavirus (HPV) 16 E6 and comprising a human variable region and a murine constant region. In an embodiment of the invention, the TCR has antigenic specificity for HPV 16 E6$_{29-38}$.

The HPV 16 is the subtype of HPV that is most commonly associated with malignancy. Without being bound to a particular theory or mechanism, HPV 16 is believed to cause cancer at least partly through the actions of the oncoprotein E6, which deregulates cell cycle control. HPV 16 E6 is constitutively expressed in cancer cells and is not expressed by normal, uninfected human tissues. HPV 16 E6 is expressed in a variety of human cancers including, but not limited to, cancer of the uterine cervix, oropharynx, anus, anal canal, anorectum, vagina, vulva, and penis.

The TCR may have antigenic specificity for any HPV 16 E6 protein, polypeptide or peptide. In an embodiment of the invention, the TCR has antigenic specificity for a HPV 16 E6 protein comprising, consisting of, or consisting essentially of, the amino acid sequence of SEQ ID NO: 1. In a preferred embodiment of the invention, the TCR has antigenic specificity for a HPV 16 E6$_{29-38}$ peptide comprising, consisting of, or consisting essentially of, the amino acid sequence of TIHDIILECV (SEQ ID NO: 2).

In an embodiment of the invention, the inventive TCRs are able to recognize HPV 16 E6 in a major histocompatibility complex (MHC) class I-dependent manner. "MHC class I-dependent manner," as used herein, means that the TCR elicits an immune response upon binding to HPV 16 E6 within the context of an MHC class I molecule. The MHC class I molecule can be any MHC class I molecule known in the art, e.g., HLA-A molecules. In a preferred embodiment of the invention, the MHC class I molecule is an HLA-A2 molecule.

The TCRs (including functional portions and functional variants thereof) of the invention provide many advantages, including when expressed by cells used for adoptive cell transfer. Without being bound by a particular theory or mechanism, it is believed that because HPV 16 E6 is expressed by HPV 16-infected cells of multiple cancer types, the inventive TCRs (including functional portions and functional variants thereof) advantageously provide the ability to destroy cells of multiple types of HPV 16-associated cancer and, accordingly, treat or prevent multiple types of HPV 16-associated cancer. Additionally, without being bound to a particular theory or mechanism, it is believed that because the HPV 16 E6 protein is expressed only in cancer cells, HPV 16-infected cells, or HPV-positive premalignancy cells, the inventive TCRs (including functional portions and functional variants thereof) advantageously target the destruction of cancer cells, HPV 16-infected cells, or HPV-positive premalignancy cells, while minimizing or eliminating the destruction of normal, non-cancerous, non-HPV-infected, and non-HPV-positive premalignant cells, thereby reducing, for example, by minimizing or eliminating, toxicity. Moreover, the inventive TCRs may, advantageously, successfully treat or prevent HPV-positive cancers that do not respond to other types of treatment such as, for example, chemotherapy alone, surgery, or radiation. Additionally, the inventive TCRs provide highly avid recognition of HPV 16 E6, which may, advantageously, provide the ability to recognize unmanipulated tumor cells (e.g., tumor cells that have not been treated with interferon-gamma, transfected with a vector encoding one or both of HPV 16 E6 and HLA-A2, pulsed with the E6$_{29-38}$ peptide, or a combination thereof).

The phrase "antigenic specificity," as used herein, means that the TCR can specifically bind to and immunologically recognize HPV 16 E6 with high avidity. For example, a TCR may be considered to have "antigenic specificity" for HPV 16 E6 if T cells expressing the TCR secrete at least about 200 pg/mL or more (e.g., 200 pg/mL or more, 300 pg/mL or more, 400 pg/mL or more, 500 pg/mL or more, 600 pg/mL or more, 700 pg/mL or more, 1000 pg/mL or more, 5,000 pg/mL or more, 7,000 pg/mL or more, 10,000 pg/mL or more, or 20,000 pg/mL or more) of interferon gamma (IFN-γ) upon co-culture with antigen-negative HLA-A2+ target cells pulsed with a low concentration of HPV 16 E6 peptide (e.g., about 0.05 ng/mL to about 5 ng/mL, 0.05 ng/mL, 0.1 ng/mL, 0.5 ng/mL, 1 ng/mL, or 5 ng/mL).

Alternatively or additionally, a TCR may be considered to have "antigenic specificity" for HPV 16 E6 if T cells expressing the TCR secrete at least twice as much IFN-γ as the untransduced peripheral blood lymphocyte (PBL) background level of IFN-γ upon co-culture with antigen-negative HLA-A2+ target cells pulsed with a low concentration of HPV 16 E6 peptide. Cells expressing the inventive TCRs (including functional portions and functional variants thereof) may also secrete IFN-γ upon co-culture with antigen-negative HLA-A2+ target cells pulsed with higher concentrations of HPV 16 E6 peptide.

The invention provides a TCR comprising two polypeptides (i.e., polypeptide chains), such as an alpha (u) chain of a TCR, a beta (0) chain of a TCR, a gamma (γ) chain of a TCR, a delta (6) chain of a TCR, or a combination thereof. The polypeptides of the inventive TCR can comprise any amino acid sequence, provided that the TCR has antigenic specificity for HPV 16 E6.

In an embodiment of the invention, the TCR comprises two polypeptide chains, each of which comprises a human variable region comprising a complementarity determining region (CDR)1, a CDR2, and a CDR3 of a TCR. In an embodiment of the invention, the TCR comprises a first polypeptide chain comprising a CDR1 comprising the amino acid sequence of SEQ ID NO: 3 (CDR1 of α chain), a CDR2 comprising the amino acid sequence of SEQ ID NO: 4 (CDR2 of α chain), and a CDR3 comprising the amino acid sequence of SEQ ID NO: 5 (CDR3 of α chain), and a second polypeptide chain comprising a CDR1 comprising the amino acid sequence of SEQ ID NO: 6 (CDR1 of β chain), a CDR2 comprising the amino acid sequence of SEQ ID NO: 7 (CDR2 of β chain), and a CDR3 comprising the amino acid sequence of SEQ ID NO: 8 (CDR3 of β chain). In this regard, the inventive TCR can comprise any one or more of the amino acid sequences selected from the group consisting of SEQ ID NOs: 3-8. Preferably, the TCR comprises the amino acid sequences of SEQ ID NOs: 3-5 or SEQ ID NOs: 6-8. In an especially preferred embodiment, the TCR comprises the amino acid sequences of SEQ ID NOs: 3-8.

In an embodiment of the invention, the TCR can comprise an amino acid sequence of a variable region of a TCR comprising the CDRs set forth above. In this regard, the TCR can comprise the amino acid sequence of SEQ ID NO: 9 (the variable region of an α chain), SEQ ID NO: 10 (the variable region of a β chain), or both SEQ ID NOs: 9 and 10. Preferably, the inventive TCR comprises the amino acid sequences of both SEQ ID NOs: 9 and 10.

The inventive TCRs may further comprise a constant region derived from any suitable species such as, e.g., human or mouse. In an embodiment of the invention, the inventive TCRs further comprise a murine constant region. In this regard, the TCR can comprise the amino acid sequence of SEQ ID NO: 15 (the constant region of a murine α chain), SEQ ID NO: 16 (the constant region of a murine β chain), or both SEQ ID NOs: 15 and 16. In a preferred embodiment, the inventive TCRs are chimeric TCRs comprising both a human variable region and a murine constant region.

In an embodiment of the invention, the inventive chimeric TCR may comprise a combination of a variable region and a constant region. In this regard, the TCR can comprise an alpha chain comprising the amino acid sequences of both SEQ ID NO: 9 (the variable region of a human α chain) and SEQ ID NO: 15 (the constant region of a murine α chain), a beta chain comprising the amino acid sequence of both SEQ ID NO: 10 (the variable region of a human β chain) and SEQ ID NO: 16 (the constant region of a murine β chain), or all of the amino acid sequences of SEQ ID NOs: 9-10 and 15-16.

As used herein, the term "murine" or "human," when referring to a TCR or any component of a TCR described herein (e.g., complementarity determining region (CDR), variable region, constant region, alpha chain, and/or beta chain), means a TCR (or component thereof) which is derived from a mouse or a human, respectively, i.e., a TCR (or component thereof) that originated from or was, at one time, expressed by a mouse T cell or a human T cell, respectively.

In an embodiment of the invention, the chimeric TCR can comprise an α chain of a TCR and a β chain of a TCR. Each of the α chain and β chain of the inventive chimeric TCR can independently comprise any amino acid sequence. Preferably, the α chain comprises the human variable region of an α chain and the murine constant region of an α chain as set forth above. In this regard, the inventive chimeric TCR can comprise the amino acid sequence of SEQ ID NO: 17. An α chain of this type can be paired with any β chain of a TCR. Preferably, the β chain of the inventive chimeric TCR comprises the human variable region of a β chain and the murine constant region of a β chain as set forth above. In this regard, the inventive chimeric TCR can comprise the amino acid sequence of SEQ ID NO: 18. The inventive chimeric TCR, therefore, can comprise the amino acid sequence of SEQ ID NO: 17, SEQ ID NO: 18, or both SEQ ID NOs: 17 and 18. Preferably, the inventive chimeric TCR comprises the amino acid sequences of both SEQ ID NOs: 17 and 18.

In an embodiment of the invention, the TCR is a human TCR. The human TCR may comprise any of the CDR regions as described herein with respect to other aspects of the invention. In this regard, an embodiment of the invention provides an isolated or purified TCR having antigenic specificity for HPV 16 E6 and comprising the amino acid sequences of SEQ ID NOs: 3-8. In another embodiment of the invention, the human TCR may comprise any of the variable regions described herein with respect to other aspects of the invention.

In an embodiment of the invention, the inventive human TCRs further comprise a human constant region. In this regard, the human TCR can comprise the amino acid sequence of SEQ ID NO: 13 (the constant region of a human α chain), SEQ ID NO: 14 (the constant region of a human β chain), or both SEQ ID NOs: 13 and 14.

In an embodiment of the invention, the inventive human TCR may comprise a combination of a variable region and a constant region. In this regard, the TCR can comprise an alpha chain comprising the amino acid sequences of both SEQ ID NO: 9 (the variable region of a human α chain) and SEQ ID NO: 13 (the constant region of a human α chain), a beta chain comprising the amino acid sequences of both SEQ ID NO: 10 (the variable region of a human β chain) and SEQ ID NO: 14 (the constant region of a human β chain), or all of the amino acid sequences of SEQ ID NOs: 9-10 and 13-14.

In an embodiment of the invention, the human TCR can comprise an α chain of a TCR and a β chain of a TCR. Each of the α chain and β chain of the inventive human TCR can independently comprise any amino acid sequence. Preferably, the α chain comprises the human variable region of an α chain and the human constant region of an α chain as set forth above. In this regard, the inventive human TCR can comprise the amino acid sequence of SEQ ID NO: 11. An α chain of this type can be paired with any β chain of a TCR. Preferably, the β chain of the inventive human TCR comprises the human variable region of a β chain and the human constant region of a β chain as set forth above. In this regard, the inventive human TCR can comprise the amino acid sequence of SEQ ID NO: 12. The inventive human TCR, therefore, can comprise the amino acid sequence of SEQ ID NO: 11, SEQ ID NO: 12, or both SEQ ID NOs: 11 and 12. Preferably, the inventive human TCR comprises the amino acid sequences of both SEQ ID NOs: 11 and 12.

Also provided by the invention is a polypeptide comprising a functional portion of any of the TCRs (or functional variants thereof) described herein. The term "polypeptide" as used herein includes oligopeptides and refers to a single chain of amino acids connected by one or more peptide bonds.

With respect to the inventive polypeptides, the functional portion can be any portion comprising contiguous amino acids of the TCR (or functional variant thereof) of which it is a part, provided that the functional portion specifically binds to HPV 16 E6. The term "functional portion" when used in reference to a TCR (or functional variant thereof) refers to any part or fragment of the TCR (or functional variant thereof) of the invention, which part or fragment retains the biological activity of the TCR (or functional variant thereof) of which it is a part (the parent TCR or parent functional variant thereof). Functional portions encompass, for example, those parts of a TCR (or functional variant thereof) that retain the ability to specifically bind to HPV 16 E6 (e.g., in an HLA-A2-dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR (or functional variant thereof).

The functional portion can comprise additional amino acids at the amino or carboxy terminus of the portion, or at both termini, which additional amino acids are not found in the amino acid sequence of the parent TCR or functional variant thereof. Desirably, the additional amino acids do not interfere with the biological function of the functional portion, e.g., specifically binding to HPV 16 E6; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and CDR3 of the variable region(s) of the α chain and/or β chain of a TCR or functional variant thereof of the invention. In an embodiment of the invention, the polypeptide can comprise a functional portion comprising the amino acid sequence of SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), or a combination thereof. Preferably, the inventive polypeptide comprises a functional portion comprising the amino acid sequences of SEQ ID NOs: 3-5; 6-8; or all of SEQ ID NOs: 3-8. More preferably, the polypeptide comprises a functional portion comprising the amino acid sequences of all of SEQ ID NOs: 3-8.

In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of SEQ ID NO: 9 (the variable region of an α chain), SEQ ID NO: 10 (the variable region of α chain), or both SEQ ID NOs: 9 and 10. Preferably, the polypeptide comprises the amino acid sequences of both SEQ ID NOs: 9 and 10.

The inventive polypeptide may further comprise a constant region derived from any suitable species such as, e.g., human or mouse. In this regard, the polypeptide can comprise the amino acid sequence of SEQ ID NO: 13 (the constant region of a human α chain), SEQ ID NO: 14 (the constant region of a human β chain), SEQ ID NO: 15 (the constant region of a murine α chain), SEQ ID NO: 16 (the constant region of a murine β chain), both SEQ ID NOs: 13 and 14, or both SEQ ID NOs: 15 and 16. Preferably, the polypeptide comprises the amino acid sequences of both SEQ ID NOs: 13 and 14 or both SEQ ID NOs: 15 and 16.

In an embodiment of the invention, the inventive polypeptide may comprise a combination of a variable region and a constant region. In this regard, the polypeptide can comprise the amino acid sequences of both SEQ ID NOs: 9 and 15, both SEQ ID NOs: 9 and 13, both SEQ ID NOs: 10 and 16, both SEQ ID NOs: 10 and 14, all of SEQ ID NOs: 9-10 and 15-16, or all of SEQ ID NOs: 9-10 and 13-14.

In an embodiment of the invention, the inventive polypeptide can comprise the entire length of an α or β chain of one of the TCRs or functional variant thereof described herein. In this regard, the inventive polypeptide can comprise an amino acid sequence of SEQ ID NOs: 11, 12, 17, or 18. Alternatively, the polypeptide of the invention can comprise α and β chains of the TCRs or functional variants thereof described herein. For example, the inventive polypeptide can comprise the amino acid sequences of both SEQ ID NOs: 11 and 12 or both SEQ ID NOs: 17 and 18, both SEQ ID NOs: 11 and 18, or both SEQ ID NOs: 17 and 12. Preferably, the polypeptide comprises the amino acid sequences of both SEQ ID NOs: 11 and 12 or both SEQ ID NOs: 17 and 18.

The invention further provides a protein comprising at least one of the polypeptides described herein. By "protein" is meant a molecule comprising one or more polypeptide chains.

In an embodiment, the protein of the invention can comprise a first polypeptide chain comprising the amino acid sequences of SEQ ID NOs: 3-5 and a second polypeptide chain comprising the amino acid sequence of SEQ ID NOs: 6-8. Alternatively or additionally, the protein of the invention can comprise a first polypeptide chain comprising the amino acid sequence of SEQ ID NO: 9, and a second polypeptide chain comprising the amino acid sequence of SEQ ID NO: 10. The protein of the invention can, for example, comprise a first polypeptide chain comprising the amino acid sequence of both SEQ ID NO: 9 and 13 or both SEQ ID NOs: 9 and 15, and a second polypeptide chain comprising the amino acid sequence of both SEQ ID NOs: 10 and 14 or both SEQ ID NOs: 10 and 16. The protein of the invention can, for example, comprise a first polypeptide chain comprising the amino acid sequence of SEQ ID NO: 11 or 17, and a second polypeptide chain comprising the amino acid sequence of SEQ ID NO: 12 or 18. In this instance, the protein of the invention can be a TCR. Alternatively, if, for example, the protein comprises a single polypeptide chain comprising the amino acid sequences of SEQ ID NO: 11 and 12 or SEQ ID NO: 17 and 18, or if the first and/or second polypeptide chain(s) of the protein further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide can encode any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. See, for instance, Choi et al., Mol. Biotechnol. 31: 193-202 (2005).

In some embodiments of the invention, the TCRs (and functional portions and functional variants thereof), polypeptides, and proteins of the invention may be expressed as a single protein comprising a linker peptide linking the α chain and the β chain. In this regard, the TCRs (and functional variants and functional portions thereof), polypeptides, and proteins of the invention comprising the amino acid sequences of SEQ ID NO: 11 and 12 or SEQ ID NO: 17 and 18 may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. For example, the linker peptide may comprise the amino acid sequence of SEQ ID NO: 37. Upon expression of the construct including the linker peptide by a host cell, the linker peptide may be cleaved, resulting in separated α and β chains.

The protein of the invention can be a recombinant antibody comprising at least one of the inventive polypeptides described herein. As used herein, "recombinant antibody" refers to a recombinant (e.g., genetically engineered) protein comprising at least one of the polypeptides of the invention and a polypeptide chain of an antibody, or a portion thereof. The polypeptide of an antibody, or portion thereof, can be a heavy chain, a light chain, a variable or constant region of a heavy or light chain, a single chain variable fragment (scFv), or an Fc, Fab, or F(ab)$_2$' fragment of an antibody, etc. The polypeptide chain of an antibody, or portion thereof, can exist as a separate polypeptide of the recombinant antibody. Alternatively, the polypeptide chain of an antibody, or portion thereof, can exist as a polypeptide, which is expressed in frame (in tandem) with the polypeptide of the invention. The polypeptide of an antibody, or portion thereof, can be a polypeptide of any antibody or any antibody fragment, including any of the antibodies and antibody fragments described herein.

Included in the scope of the invention are functional variants of the inventive TCRs described herein. The term "functional variant" as used herein refers to a TCR, polypeptide, or protein having substantial or significant sequence identity or similarity to a parent TCR, polypeptide, or protein, which functional variant retains the biological activity of the TCR, polypeptide, or protein of which it is a variant. Functional variants encompass, for example, those variants of the TCR, polypeptide, or protein described herein (the parent TCR, polypeptide, or protein) that retain the ability to specifically bind to HPV 16 E6 for which the parent TCR has antigenic specificity or to which the parent polypeptide or protein specifically binds, to a similar extent, the same extent, or to a higher extent, as the parent TCR, polypeptide, or protein. In reference to the parent TCR, polypeptide, or protein, the functional variant can, for instance, be at least about 30%, 50%, 75%, 80%, 90%, 95%, 96%, 97%, 98%, 99% or more identical in amino acid sequence to the parent TCR, polypeptide, or protein.

The functional variant can, for example, comprise the amino acid sequence of the parent TCR, polypeptide, or protein with at least one conservative amino acid substitution. Conservative amino acid substitutions are known in the art, and include amino acid substitutions in which one amino acid having certain physical and/or chemical properties is exchanged for another amino acid that has the same chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

Alternatively or additionally, the functional variants can comprise the amino acid sequence of the parent TCR, polypeptide, or protein with at least one non-conservative amino acid substitution. In this case, it is preferable for the non-conservative amino acid substitution to not interfere with or inhibit the biological activity of the functional variant. Preferably, the non-conservative amino acid substitution enhances the biological activity of the functional variant, such that the biological activity of the functional variant is increased as compared to the parent TCR, polypeptide, or protein.

The TCR (or functional variant thereof), polypeptide, or protein can consist essentially of the specified amino acid sequence or sequences described herein, such that other components of the TCR (or functional variant thereof), polypeptide, or protein, e.g., other amino acids, do not materially change the biological activity of the TCR (or functional variant thereof), polypeptide, or protein. In this regard, the inventive TCR (or functional variant thereof), polypeptide, or protein can, for example, consist essentially of the amino acid sequence of SEQ ID NO: 11, 12, 17, or 18, both SEQ ID NOs: 11 and 12, both SEQ ID NOs: 17 and 18, both SEQ ID NOs: 11 and 18, or both SEQ ID NOs: 17 and 12. Also, for instance, the inventive TCRs (including functional variants thereof), polypeptides, or proteins can consist essentially of the amino acid sequence(s) of SEQ ID NO: 9, 10, or both SEQ ID NOs: 9 and 10. Furthermore, the inventive TCRs (including functional variants thereof), polypeptides, or proteins can consist essentially of the amino acid sequence of SEQ ID NO: 3 (CDR1 of α chain), SEQ ID NO: 4 (CDR2 of α chain), SEQ ID NO: 5 (CDR3 of α chain), SEQ ID NO: 6 (CDR1 of β chain), SEQ ID NO: 7 (CDR2 of β chain), SEQ ID NO: 8 (CDR3 of γ chain), or any combination thereof, e.g., SEQ ID NOs: 3-5; 6-8; or 3-8.

The TCRs, polypeptides, and proteins of the invention (including functional variants thereof) can be of any length, i.e., can comprise any number of amino acids, provided that the TCRs, polypeptides, or proteins (or functional variants thereof) retain their biological activity, e.g., the ability to specifically bind to HPV 16 E6; detect cancer, HPV 16 infection, or HPV-positive premalignancy in a mammal; or treat or prevent cancer, HPV 16 infection, or HPV-positive premalignancy in a mammal, etc. For example, the polypeptide can be in the range of from about 50 to about 5000 amino acids long, such as 50, 70, 75, 100, 125, 150, 175, 200, 300, 400, 500, 600, 700, 800, 900, 1000 or more amino acids in length. In this regard, the polypeptides of the invention also include oligopeptides.

The TCRs, polypeptides, and proteins of the invention (including functional variants thereof) of the invention can comprise synthetic amino acids in place of one or more naturally-occurring amino acids. Such synthetic amino acids are known in the art, and include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The TCRs, polypeptides, and proteins of the invention (including functional variants thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The TCR, polypeptide, and/or protein of the invention (including functional variants thereof) can be obtained by methods known in the art. Suitable methods of de novo synthesizing polypeptides and proteins are described in references, such as Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; and U.S. Pat. No. 5,449,752. Also, polypeptides and proteins can be recombinantly produced using the nucleic acids described herein using standard recombinant methods. See, for instance, Green and Sambrook, *Molecular Cloning: A Laboratory Manual*, 4$^{th}$ ed., Cold Spring Harbor Press, Cold Spring Harbor, N Y 2012; and Ausubel et al., *Current Protocols in Molecular Biology*, Greene Publishing Associates and John Wiley & Sons, N Y, 1994. Further, some of the TCRs, polypeptides, and proteins of the invention (including functional variants thereof) can be isolated and/or purified from a source, such as a plant, a bacterium, an insect, a mammal, e.g., a rat, a human, etc. Methods of isolation and purification are well-known in the art. Alternatively, the TCRs, polypeptides, and/or proteins described herein (including functional variants thereof) can be commercially synthesized by companies, such as Synpep (Dublin, CA), Peptide Technologies Corp. (Gaithersburg, MD), and Multiple Peptide Systems (San Diego, CA). In this respect, the inventive TCRs (including functional variants thereof), polypeptides, and proteins can be synthetic, recombinant, isolated, and/or purified.

Included in the scope of the invention are conjugates, e.g., bioconjugates, comprising any of the inventive TCRs, polypeptides, or proteins (including any of the functional variants thereof), nucleic acids, recombinant expression vectors, host cells, populations of host cells, or antibodies, or antigen binding portions thereof. Conjugates, as well as methods of synthesizing conjugates in general, are known in the art (See, for instance, Hudecz, F., *Methods Mol. Biol.* 298: 209-223 (2005) and Kirin et al., *Inorg Chem.* 44(15): 5405-5415 (2005)).

An embodiment of the invention provides a nucleic acid comprising a nucleotide sequence that encodes any of the TCRs, polypeptides, and proteins herein. By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In an embodiment, the nucleic acid comprises complementary DNA (cDNA). It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

The nucleic acids can be constructed based on chemical synthesis and/or enzymatic ligation reactions using procedures known in the art. See, for example, Green and Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Macromolecular Resources (Fort Collins, CO) and Synthegen (Houston, TX).

The nucleic acid can comprise any nucleotide sequence which encodes any of the TCRs, polypeptides, proteins, or functional variants thereof described herein. In an embodiment of the invention, the nucleotide sequence may comprise, consist, or consist essentially of all of SEQ ID NOs: 31-36 (encoding CDR1α, CDR2α, CDR3α, CDR1β, CDR2β, CDR3β, respectively); all of SEQ ID NOs: 31-33; all of SEQ ID NOs: 34-36; both of SEQ ID NOs: 19-20 (encoding variable regions of α and β chains, respectively); both of SEQ ID NOs: 23-24 (encoding human constant region of α and β chains, respectively); both of SEQ ID NOs: 25-26 (encoding murine constant region of α and β chains, respectively), all of SEQ ID NOs: 19-20 and 23-24, all of SEQ ID NOs: 19-20 and 25-26, both of SEQ ID NOs: 21-22 (encoding human α and β chains, respectively), or both of SEQ ID NOs: 27-28 (encoding chimeric α and β chains, respectively). In another embodiment of the invention, the nucleotide sequence may comprise, consist, or consist essentially of any one of SEQ ID NOs: 19-28 and 31-36.

In an embodiment of the invention, the nucleic acid comprises a non-natural nucleotide sequence. A nucleotide sequence may be considered to be "non-natural" if the nucleotide sequence is not found in nature. In some embodiments, the nucleotide sequence may be codon-optimized. Without being bound to a particular theory or mechanism, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency. In an embodiment of the invention, the codon-optimized nucleotide sequence may comprise, consist, or consist essentially of SEQ ID NO: 38 (variable region of α chain), SEQ ID NO: 39 (variable region of β chain), or SEQ ID NOs: 38 and 39.

The invention also provides a nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions preferably hybridizes under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive TCRs (including functional portions and functional variants thereof). It is generally appreciated that conditions can be rendered more stringent by the addition of increasing amounts of formamide.

The invention also provides a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

The nucleic acids of the invention can be incorporated into a recombinant expression vector. In this regard, the invention provides recombinant expression vectors comprising any of the nucleic acids of the invention. In an embodiment of the invention, the recombinant expression vector comprises a nucleotide sequence encoding the α chain, the β chain, and linker peptide. For example, in an embodiment, the recombinant expression vector comprises a codon-optimized nucleotide sequence comprising SEQ ID NO: 29 (encoding chimeric α and β chains SEQ ID NOs: 17 and 18 with a linker positioned between them).

For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors of the invention are not naturally-occurring as a whole. However, parts of the vectors can be naturally-occurring. The inventive recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring, non-naturally-occurring internucleotide linkages, or both types of linkages. Preferably, the non-naturally occurring or altered nucleotides or internucleotide linkages does not hinder the transcription or replication of the vector.

The recombinant expression vector of the invention can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA). Bacteriophage vectors, such as λGT10, λGT11, λZapII (Stratagene), λEMBL4, and λNM1149, also can be used. Examples of plant expression vectors include pBI01, pBI101.2, pBI101.3, pBI121 and pBIN19 (Clontech). Examples of animal expression vectors include pEUK-Cl, pMAM and pMAMneo (Clontech). Preferably, the recombinant expression vector is a viral vector, e.g., a retroviral vector. In an especially preferred embodiment, the recombinant expression vector is an MSGV1 vector. In an embodiment, an MSGV1 vector comprising a codon-optimized nucleotide sequence encoding a chimeric TCR comprising SEQ ID NOs: 17 and 18 of the invention comprises the nucleotide sequence of SEQ ID NO: 30.

The recombinant expression vectors of the invention can be prepared using standard recombinant DNA techniques described in, for example, Green and Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2µ plasmid, λ, SV40, bovine papillomavirus, and the like.

Desirably, the recombinant expression vector comprises regulatory sequences, such as transcription and translation initiation and termination codons, which are specific to the type of host cell (e.g., bacterium, fungus, plant, or animal) into which the vector is to be introduced, as appropriate and taking into consideration whether the vector is DNA- or RNA-based.

The recombinant expression vector can include one or more marker genes, which allow for selection of transformed or transfected host cells. Marker genes include biocide resistance, e.g., resistance to antibiotics, heavy metals, etc., complementation in an auxotrophic host cell to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the TCR, polypeptide, or protein (including functional variants thereof), or to the nucleotide sequence which is complementary to or which hybridizes to the nucleotide sequence encoding the TCR, polypeptide, or protein (including functional variants thereof). The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression. Further, the recombinant expression vectors can be made to include a suicide gene.

As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, *Suicide Gene Therapy: Methods and Reviews*, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

Another embodiment of the invention further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5α *E. coli* cells, Chinese hamster ovarian cells, monkey VERO cells, COS cells, HEK293 cells, and the like. For purposes of amplifying or replicating the recombinant expression vector, the host cell is preferably a prokaryotic cell, e.g., a DH5α cell. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood lymphocyte (PBL) or a peripheral blood mononuclear cell (PBMC). More preferably, the host cell is a T cell.

For purposes herein, the T cell can be any T cell, such as a cultured T cell, e.g., a primary T cell, or a T cell from a cultured T cell line, e.g., Jurkat, SupT1, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, $CD4^+$/$CD8^+$ double positive T cells, $CD4^+$ helper T cells, e.g., $Th_1$ and $Th_2$ cells, $CD4^+$ T cells, $CD8^+$ T cells (e.g., cytotoxic T cells), tumor infiltrating lymphocytes (TILs), memory T cells (e.g., central memory T cells and effector memory T cells), naïve T cells, and the like.

Also provided by the invention is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cells, a muscle cell, a brain cell, etc. Alternatively, the population of cells can be a substantially homogeneous population, in which the population comprises mainly of host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

In an embodiment of the invention, the numbers of cells in the population may be rapidly expanded. Expansion of the numbers of T cells can be accomplished by any of a number of methods as are known in the art as described in, for example, U.S. Pat. Nos. 8,034,334; 8,383,099; U.S. Patent Application Publication No. 2012/0244133; Dudley et al., *J. Immunother.*, 26:332-42 (2003); and Riddell et al., *J. Immunol. Methods*, 128:189-201 (1990).

The invention further provides an antibody, or antigen binding portion thereof, which specifically binds to a functional portion of any of the TCRs (or functional variant thereof) described herein. Preferably, the functional portion specifically binds to the cancer antigen, e.g., the functional portion comprising the amino acid sequence SEQ ID NO: 3 (CDR1 of α chain), 4 (CDR2 of α chain), 5 (CDR3 of α chain), 6 (CDR1 of β chain), 7 (CDR2 of β chain), 8 (CDR3 of β chain), SEQ ID NO: 9 (variable region of α chain), SEQ ID NO: 10 (variable region of β chain), or a combination thereof, e.g., 3-5; 6-8; 3-8; 9; 10; or 9-10. More preferably, the functional portion comprises the amino acid sequences of SEQ ID NOs: 3-8 or SEQ ID NOs: 9 and 10. In a preferred embodiment, the antibody, or antigen binding portion thereof, binds to an epitope which is formed by all 6 CDRs (CDR1-3 of the alpha chain and CDR1-3 of the beta chain). The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form. Also, the antibody can have any level of affinity or avidity for the functional portion of the inventive TCR (or functional variant thereof). Desirably, the antibody is specific for the functional portion of the inventive TCR (or functional variants thereof), such that there is minimal cross-reaction with other peptides or proteins.

Methods of testing antibodies for the ability to bind to any functional portion or functional variant of the inventive TCR are known in the art and include any antibody-antigen binding assay, such as, for example, radioimmunoassay (RIA), ELISA, Western blot, immunoprecipitation, and competitive inhibition assays (see, e.g., Janeway et al., infra, and U.S. Patent Application Publication No. 2002/0197266 A1).

Suitable methods of making antibodies are known in the art. For instance, standard hybridoma methods are described in, e.g., Köhler and Milstein, *Eur. J. Immunol.*, 5, 511-519 (1976), Harlow and Lane (eds.), *Antibodies: A Laboratory Manual*, CSH Press (1988), and C. A. Janeway et al. (eds.), *Immunobiology*, 8$^{th}$ Ed., Garland Publishing, New York, NY (2011)). Alternatively, other methods, such as EBV-hybridoma methods (Haskard and Archer, *J. Immunol. Methods*, 74(2), 361-67 (1984), and Roder et al., *Methods Enzymol.*, 121, 140-67 (1986)), and bacteriophage vector expression systems (see, e.g., Huse et al., *Science*, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266 A1.

Phage display furthermore can be used to generate the antibody of the invention. In this regard, phage libraries encoding antigen-binding variable (V) domains of antibodies can be generated using standard molecular biology and recombinant DNA techniques (see, e.g., Green and Sambrook et al. (eds.), *Molecular Cloning, A Laboratory Manual*, 4$^{th}$ Edition, Cold Spring Harbor Laboratory Press, New York (2012)). Phage encoding a variable region with the desired specificity are selected for specific binding to the desired antigen, and a complete or partial antibody is reconstituted comprising the selected variable domain. Nucleic acid sequences encoding the reconstituted antibody are introduced into a suitable cell line, such as a myeloma cell used for hybridoma production, such that antibodies having the characteristics of monoclonal antibodies are secreted by the cell (see, e.g., Janeway et al., supra, Huse et al., supra, and U.S. Pat. No. 6,265,150).

Antibodies can be produced by transgenic mice that are transgenic for specific heavy and light chain immunoglobulin genes. Such methods are known in the art and described in, for example U.S. Pat. Nos. 5,545,806 and 5,569,825, and Janeway et al., supra.

Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in, for example, U.S. Pat. No. 5,639,641 and Pedersen et al., *J. Mol. Biol.*, 235, 959-973 (1994).

The invention also provides antigen binding portions of any of the antibodies described herein. The antigen binding portion can be any portion that has at least one antigen binding site, such as Fab, F(ab')$_2$, dsFv, sFv, diabodies, and triabodies.

A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering*, 7, 697-704 (1994)). Antibody fragments of the invention, however, are not limited to these exemplary types of antibody fragments.

Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

The inventive TCRs, polypeptides, proteins, (including functional variants thereof), nucleic acids, recombinant expression vectors, host cells (including populations thereof), and antibodies (including antigen binding portions thereof), can be isolated and/or purified. The term "isolated" as used herein means having been removed from its natural environment. The term "purified" as used herein means having been increased in purity, wherein "purity" is a relative term, and not to be necessarily construed as absolute purity. For example, the purity can be at least about 50%, can be greater than 60%, 70%, 80%, 90%, 95%, or can be 100%.

The inventive TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the TCRs, polypeptides, proteins, functional portions, functional variants, nucleic acids, expression vectors, host cells (including populations thereof), and antibodies (including antigen binding portions thereof) described herein, and a pharmaceutically acceptable carrier. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as a chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one which has no detrimental side effects or toxicity under the conditions of use.

The choice of carrier will be determined in part by the particular inventive TCR material, as well as by the particular method used to administer the inventive TCR material. Accordingly, there are a variety of suitable formulations of the pharmaceutical composition of the invention. Suitable formulations may include any of those for oral, parenteral, subcutaneous, intravenous, intramuscular, intraarterial, intrathecal, or interperitoneal administration. More than one route can be used to administer the inventive TCR materials, and in certain instances, a particular route can provide a more immediate and more effective response than another route.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, IL), PLASMA-LYTE A (Baxter, Deerfield, IL), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered should be sufficient to effect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

Many assays for determining an administered dose are known in the art. For purposes of the invention, an assay, which comprises comparing the extent to which target cells are lysed or IFN-γ is secreted by T cells expressing the inventive TCR (or functional variant or functional portion thereof), polypeptide, or protein upon administration of a given dose of such T cells to a mammal among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

The dose of the inventive TCR material also will be determined by the existence, nature and extent of any adverse side effects that might accompany the administration of a particular inventive TCR material. Typically, the attending physician will decide the dosage of the inventive TCR material with which to treat each individual patient, taking into consideration a variety of factors, such as age, body weight, general health, diet, sex, inventive TCR material to be administered, route of administration, and the severity of the condition being treated. In an embodiment in which the inventive TCR material is a population of cells, the number of cells administered per infusion may vary, e.g., from about $1 \times 10^6$ to about $1 \times 10^{12}$ cells or more.

One of ordinary skill in the art will readily appreciate that the inventive TCR materials of the invention can be modified in any number of ways, such that the therapeutic or prophylactic efficacy of the inventive TCR materials is increased through the modification. For instance, the inventive TCR materials can be conjugated either directly or indirectly through a bridge to a targeting moiety. The practice of conjugating compounds, e.g., inventive TCR materials, to targeting moieties is known in the art. See, for instance, Wadwa et al., *J. Drug Targeting* 3: 111 (1995) and U.S. Pat. No. 5,087,616. The term "targeting moiety" as used herein, refers to any molecule or agent that specifically recognizes and binds to a cell-surface receptor, such that the targeting moiety directs the delivery of the inventive TCR materials to a population of cells on which surface the receptor is expressed. Targeting moieties include, but are not limited to, antibodies, or fragments thereof, peptides, hormones, growth factors, cytokines, and any other natural or non-natural ligands, which bind to cell surface receptors (e.g., Epithelial Growth Factor Receptor (EGFR), T cell receptor (TCR), B-cell receptor (BCR), CD28, Platelet-derived Growth Factor Receptor (PDGF), nicotinic acetylcholine receptor (nAChR), etc.). The term "bridge" as used herein, refers to any agent or molecule that links the inventive TCR materials to the targeting moiety. One of ordinary skill in the art recognizes that sites on the inventive TCR materials, which are not necessary for the function of the inventive TCR materials, are ideal sites for attaching a bridge and/or a targeting moiety, provided that the bridge and/or targeting moiety, once attached to the inventive TCR materials, do(es) not interfere with the function of the inventive TCR materials, i.e., the ability to bind to HPV 16 E6; or to detect, treat, or prevent cancer, HPV 16 infection, or HPV-positive premalignancy.

It is contemplated that the inventive pharmaceutical compositions, TCRs (including functional variants thereof), polypeptides, proteins, nucleic acids, recombinant expression vectors, host cells, or populations of cells can be used in methods of treating or preventing cancer, HPV 16 infection, or HPV-positive premalignancy. Without being bound to a particular theory, the inventive TCRs (and functional variants thereof) are believed to bind specifically to HPV 16 E6, such that the TCR (or related inventive polypeptide or protein and functional variants thereof), when expressed by a cell, is able to mediate an immune response against a target cell expressing HPV 16 E6. In this regard, the invention provides a method of treating or preventing a condition in a mammal, comprising administering to the mammal any of the pharmaceutical compositions, TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a recombinant vector which encodes any of the TCRs (and functional variants thereof), polypeptides, or proteins described herein, in an amount effective to treat or prevent the condition in the mammal, wherein the condition is cancer, HPV 16 infection, or HPV-positive premalignancy.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, HPV 16 infection, or HPV-positive premalignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive TCRs (and functional variants thereof), polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the inventive methods, the cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is HPV 16-positive cancer. While the cancers most commonly associated with HPV 16 infection include cancer of the uterine cervix, oropharynx, anus, anal canal, anorectum, vagina, vulva, and penis, the inventive methods may be used to treat any HPV 16-positive cancer, including those that occur at other anatomical areas.

The mammal referred to in the inventive methods can be any mammal. As used herein, the term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The following examples further illustrate the invention but, of course, should not be construed as in any way limiting its scope.

Example 1

This example demonstrates the isolation of human anti-HPV 16 TCRs from tumor.

A sample of a metastatic HPV 16 E6-positive anal cancer tumor (tumor 3809) was obtained from a patient. The tumor sample was analyzed for expression of HPV 16 E6, HPV 16 E7, HPV 18 E6, and HPV 18 E7 relative to glyceraldehyde 3-phosphate dehydrogenase (GAPDH) by reverse transcriptase (RT) polymerase chain reaction (PCR). Relative expression of HPV 16 E6, HPV 16 E7, HPV 18 E6, and HPV 18 E7 was compared to that of CaSki cells, HeLa cells, and 624 cells (melanoma cell line). The results are shown in FIG. 1. As shown in FIG. 1, the tumor 3809 sample was positive for HPV 16 E6 expression.

The tumor 3809 sample was divided into 24 fragments and tumor infiltrating lymphocytes (TIL) were obtained from the various fragments. The TIL were co-cultured in a 96-well plate with autologous immature dendritic cells (DCs) which had been pulsed with HPV 16 E6 alone, HPV 16 E6 in combination with anti-class I antibody, HPV 16 E7 alone, HPV 16 E7 in combination with anti-class I antibody, gp100, or OKT3. Interferon-gamma (IFN-γ) was measured. The results are shown in FIGS. 2A and 2B. As shown in FIGS. 2A and 2B, TIL were reactive against HPV 16 E6 but not gp100 or E7. The anti-HPV 16 E6 reactivity of the TIL was blocked by anti-class I antibody.

Cells from the reactive co-culture wells were selected using anti-4-1BB magnetic beads. Rapid expansion of the numbers of selected cells was performed using the Rapid Expansion Protocol (REP) as previously described (Dudley et al. *J. Immunother.* 26:332-42 (2003) and Riddell et al. *J. Immunol. Methods* 128:189-201 (1990)). Briefly, TIL were cultured with irradiated (40 Gy) allogeneic peripheral blood mononuclear "feeder" cells in complete medium (CM) with 30 ng/mL anti-CD3 antibody and 6000 IU/mL IL-2.

Figure 3:
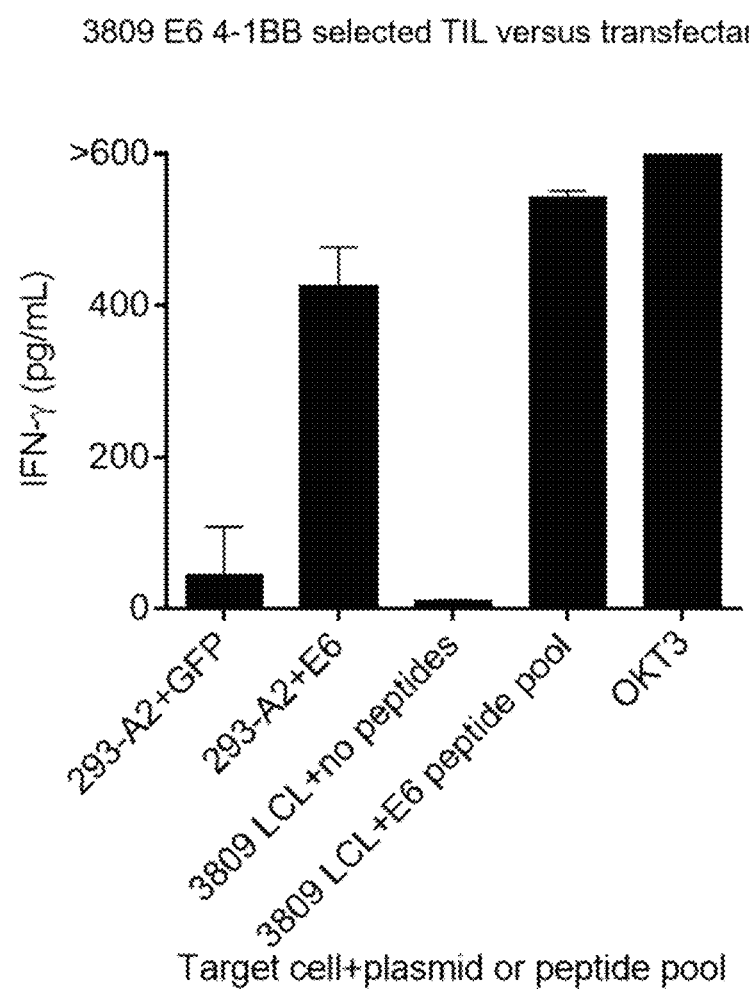
FIG. 3 is a bar graph showing IFN-γ (pg/mL) secreted by expanded numbers of 3809 4-1BB-selected TIL upon co-culture with 293-A2 cells (HEK-293 cells with stable expression of HLA-A2) transfected with green fluorescent protein (GFP), 293-A2 cells transfected with HPV 16 E6, 3809 lymphoblastoid cell line (LCL) (B cells that have been transformed using Epstein-Barr virus) cultured without peptide, 3809 LCL co-cultured with an HPV 16 E6 peptide pool, or OKT3.

The expanded numbers of 3809 4-1BB-selected cells were co-cultured with 293-A2 cells (HEK-293 cells with stable expression of HLA-A2) transfected with green fluorescent protein (GFP), 293-A2 cells transfected with E6, 3809 lymphoblastoid cell line (LCL) (B cells that have been transformed using Epstein-Barr virus) cultured without peptide, 3809 LCL co-cultured with an HPV 16 E6 peptide pool, or OKT3. The peptide pool included 15-mer peptides with 11-amino-acid overlaps that covered the complete sequence of HPV 16 E6. IFN-γ was measured. The results are shown in FIG. 3. As shown in FIG. 3, the expanded numbers of TIL were reactive against 293-A2 cells transfected with E6 but not 293-A2 cells transfected with GFP. The 3809 LCL cells co-cultured with the E6 peptide pool demonstrated reactivity while the 3809 LCL cells co-cultured with no peptides did not. Flow cytometry studies showed that the expanded numbers of cells bound to HLA-A2/E6$_{29-38}$ tetramer.

Cells were further selected by sorting using anti-4-1BB magnetic beads without further cycles of REP or cloning followed by 5' Rapid Amplification of cDNA Ends (RACE). A genotype analysis of the 5' RACE products from the magnetic bead isolation is shown in Table A. As shown in Table A, a nearly clonal population of cells was obtained.

TABLE A

| TRAV | TRAJ | Colonies | TRBV | TRBJ | TRBD | Colonies |
|---|---|---|---|---|---|---|
| TRAV35*02 | TRAJ41*01 | 4 | TRBV7-6*01 | TRBV2-3*01 | TRBD1*01 | 8 |
| TRAV10*01 | TRAJ44*01 | 3 | TRBV14*01 | TRBJ1-6*01 | TRBD1*01 | 1 |
| TRAV5*01 | TRAJ34*01 | 1 | | | | |

A nucleotide sequence comprising cDNA (SEQ ID NO: 21) encoding an alpha chain comprising the amino acid sequence of SEQ ID NO: 11 was obtained from TRAV35*02/TRAJ41*01. A nucleotide sequence comprising cDNA (SEQ ID NO: 22) encoding a beta chain comprising the amino acid sequence of SEQ ID NO: 12 was obtained from TRBV7-6*01/TRBV2-3*01/TRBD1*01.

Example 2

This example demonstrates a method of making a chimeric anti-HPV 16 TCR comprising a human variable region and a mouse constant region.

A nucleotide sequence encoding a chimeric TCR including a mouse constant region and a human variable region was prepared as follows. The nucleotide sequences encoding the original (human) constant regions of the alpha and beta chains of the TCR obtained in Example 1 (constant region amino acid sequences of SEQ ID NOs: 23 and 24, respectively) were excised and replaced with nucleotide sequences encoding a murine constant region of the alpha and beta chains, respectively. The resulting nucleotide sequences encoding the chimeric alpha and beta chains were cloned into a single nucleotide sequence with a nucleotide sequence encoding a picornavirus 2A peptide positioned between the alpha and beta chains. The combined nucleotide sequence was codon-optimized (opt) for expression in human tissues to provide a vector insert (SEQ ID NO: 29). The vector insert was cloned into an MSGV1 expression vector resulting in the nucleotide sequence of SEQ ID NO: 30 (E6 TCR). The TCR encoded by the vector comprised an alpha chain comprising an amino acid sequence comprising SEQ ID NO: 17 and a beta chain comprising an amino acid sequence comprising SEQ ID NO: 18.

Example 3

This example demonstrates that peripheral blood lymphocytes (PBL) transduced with a recombinant expression vector encoding the amino acid sequences of SEQ ID NOs: 17 and 18 specifically recognize HPV 16-positive tumor cell lines in an HLA-A2-restricted manner.

Figure 4A:
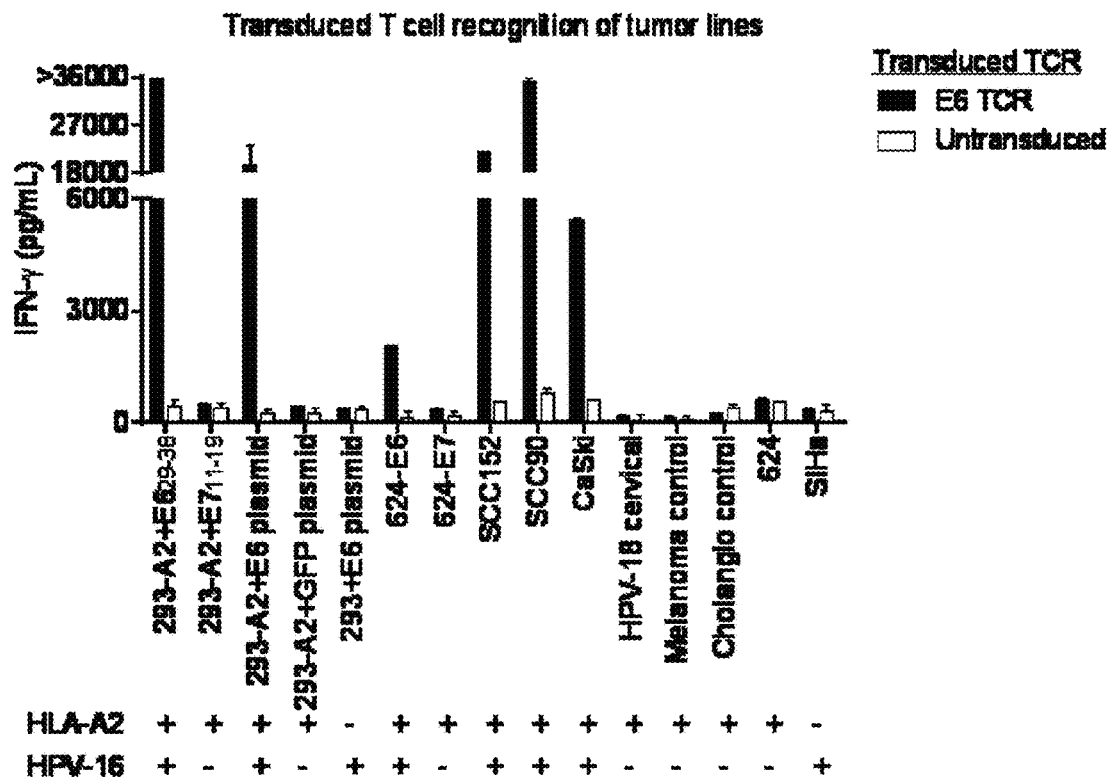
FIG. 4A is a bar graph showing IFN-γ (pg/mL) secreted by peripheral blood lymphocytes (PBL) that were not transduced (untransduced) (unshaded bars) or transduced with a nucleotide sequence encoding SEQ ID NOs: 17 and 18 (E6 TCR; shaded bars) upon co-culture with target 293-A2 cells pulsed with HPV 16 E6$_{29-38}$ peptide, 293-A2 cells pulsed with HPV 16 E711-19 peptide, 293-A2 cells transduced with a plasmid encoding HPV 16 E6, 293-A2 cells transduced with a plasmid encoding GFP, 293 cells transduced with a plasmid encoding HPV 16 E6, 624 cells transduced with a plasmid encoding HPV 16 E6, 624 cells transduced with a plasmid encoding HPV 16 E7, SCC152 cells, SCC90 cells, CaSki cells, HPV-18 cervical cancer cells, melanoma control cells, cholangio control cells, 624 cells, or SiHa cells. HLA-A2 and HPV-16 expression by each target cell is indicated in the bottom of FIG. 4A ("+" indicates positive for expression and "−" indicates negative for expression).

Peripheral blood lymphocytes (PBL) were transduced with the expression vector of Example 2 and were co-cultured with target 293-A2 cells pulsed with HPV 16 E6$_{29-38}$ peptide, 293-A2 cells pulsed with HPV 16 E711-19 peptide, 293-A2 cells transduced with a plasmid encoding HPV 16 E6, 293-A2 cells transduced with a plasmid encoding GFP, 293 cells transduced with a plasmid encoding HPV 16 E6, 624 cells transduced with a plasmid encoding HPV 16 E6, 624 cells transduced with a plasmid encoding HPV 16 E7, SCC152 cells, SCC90 cells, CaSki cells, HPV-18 cervical cancer cells, melanoma control cells, cholangio control cells, 624 cells, or SiHa cells. IFN-γ was measured. The results are shown in FIG. 4A. As shown in FIG. 4A, PBMC transduced with a recombinant expression vector encoding the amino acid sequences of SEQ ID NOs: 17 and 18 specifically recognizes HPV 16-positive tumor cell lines and other HLA-A2$^+$HPV16$^+$ targets in an HLA-A2-restricted manner.

Figure 4B:
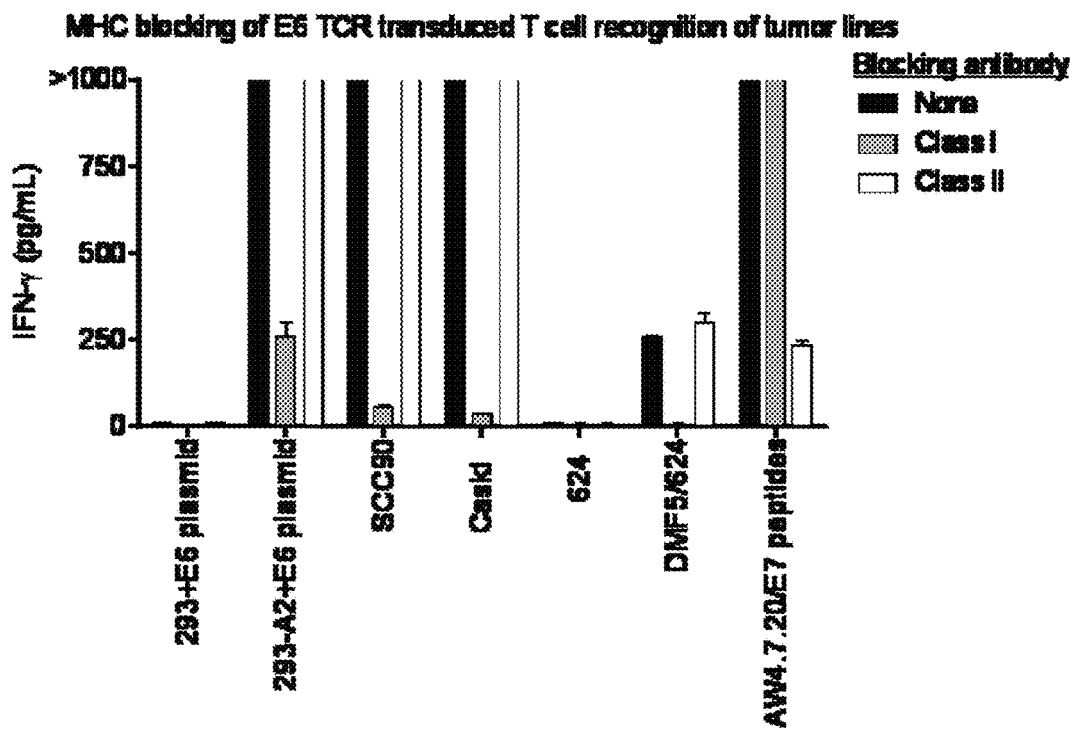
FIG. 4B is a bar graph showing IFN-γ (pg/mL) secreted by PBL transduced with a nucleotide sequence encoding SEQ ID NOs: 17 and 18 upon co-culture with target 293-A2 cells transduced with a plasmid encoding HPV 16 E6, 293 cells transduced with a plasmid encoding HPV 16 E6, SCC90 cells, CaSki cells, 624 cells, DMF/624 cells, or 4.7.20 cells pulsed with HPV 16 E7 peptides with no antibody (black bars), anti-MHC Class I antibody (grey bars), or anti-MHC Class II antibody (unshaded bars).

PBL transduced with the expression vector of Example 2 were co-cultured with target 293-A2 cells transduced with a plasmid encoding E6, 293 cells transduced with a plasmid encoding E6, SCC90 cells, CaSki cells, or 624 cells (melanoma cell line) with no antibody, anti-MHC Class I antibody, or anti-MHC Class II antibody. DMF5 (T cells transduced to express a MHC class I-restricted TCR against MART-1) were co-cultured with a melanoma cell line (624) that is recognized by DMF5 with no antibody, anti-MHC Class I antibody, or anti-MHC Class II antibody. 4.7.20 (T cells transduced to express a MHC class II-restricted TCR against HPV 16 E7) were cultured with PBMC pulsed with the E7 peptide pool "E7 peptides" with no antibody, anti-MHC Class I antibody, or anti-MHC Class II antibody. IFN-γ was measured. The results are shown in FIG. 4B. As shown in FIG. 4B, anti-MHC Class I antibody blocked the reactivity of the transduced cells against HLA-A2$^+$HPV16$^+$ targets, while anti-Class II antibody did not block reactivity.

Example 4

This example demonstrates that cells transduced with a recombinant expression vector encoding the amino acid sequences of SEQ ID NOs: 17 and 18 bind to HLA-A2-E6$_{29-38}$ tetramer in a CD8-independent manner.

PBL transduced with the recombinant expression vector of Example 2 was sorted into CD8-positive cells and CD8-negative cells by FACS. Binding to HLA- A2-E6$_{29-38}$ tetramer was measured by flow cytometry. CD8-positive and CD8-negative cells both bound to HLA-A2-E6$_{29-38}$ tetramer.

Example 5

This example demonstrates that CD4 and CD8-positive cells transduced with a recombinant expression vector encoding the amino acid sequences of SEQ ID NOs: 17 and 18 specifically recognize HPV-16 positive tumor cell lines.

Figure 5:
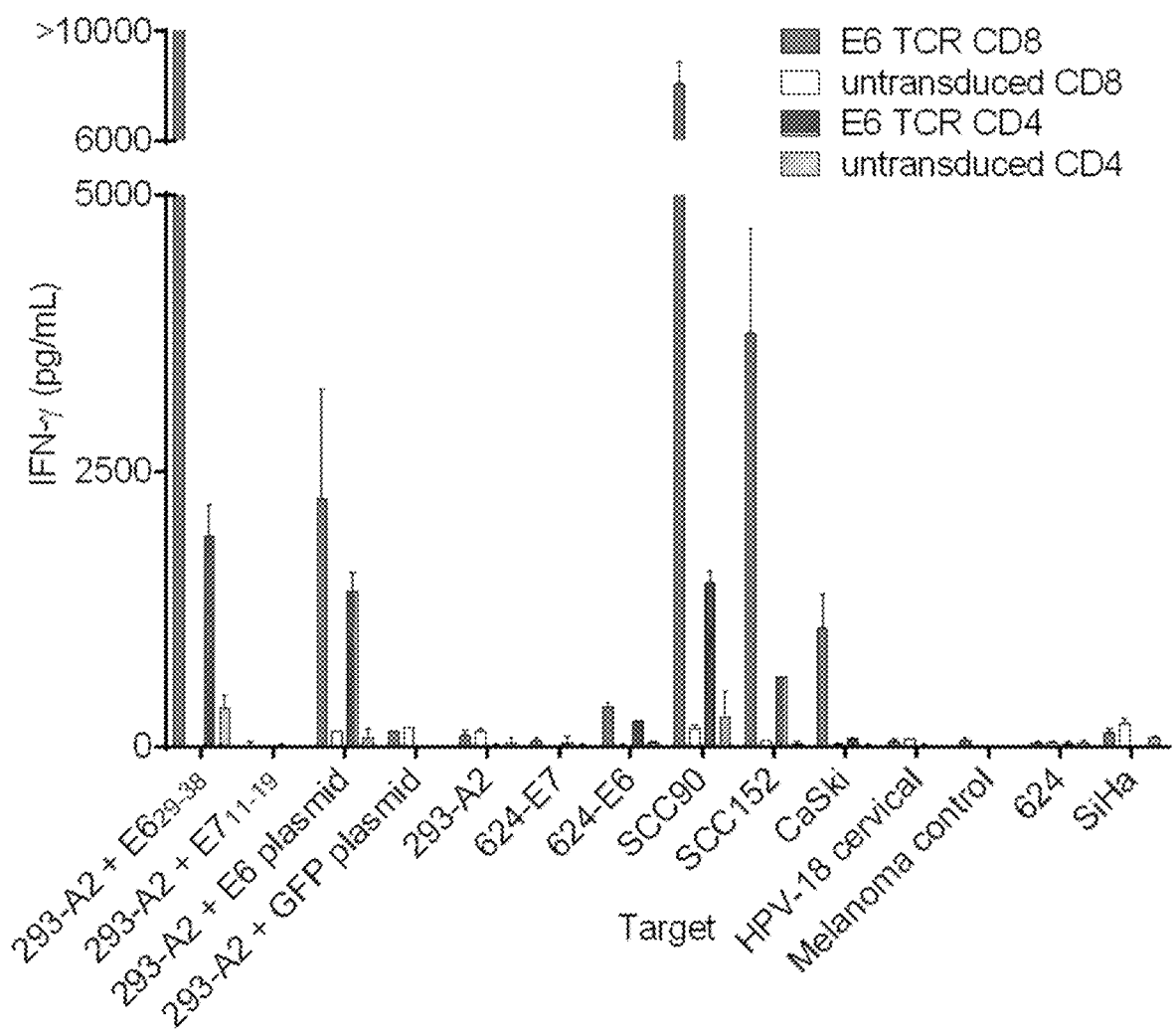
FIG. 5 is a bar graph showing IFN-γ (pg/mL) secreted by untransduced CD8-positive PBL (unshaded unhatched bars), untransduced CD4-positive PBL (cross-hatched unshaded bars), or PBL (CD8 positive (E6 TCR; shaded unhatched bars) or CD4 positive (E6 TCR; cross-hatched shaded bars)) that were transduced with a nucleotide sequence encoding SEQ ID NOs: 17 and 18 upon co-culture with target 293-A2 cells pulsed with HPV 16 E6$_{29-38}$ peptide, 293-A2 cells pulsed with HPV 16 E711-19 peptide, 293-A2 cells transduced with a plasmid encoding HPV 16 E6, 293-A2 cells transduced with a plasmid encoding GFP, 293-A2 cells, 624 cells transduced with a plasmid encoding HPV 16 E7, 624 cells transduced with a plasmid encoding HPV 16 E6, SCC152 cells, SCC90 cells, CaSki cells, HPV-cervical cancer cells, melanoma control cells, 624 cells, or SiHa cells.

CD8-positive or CD4-positive PBL were not transduced (untransduced) or transduced with the expression vector of Example 2 and were co-cultured with target 293-A2 cells pulsed with HPV 16 E6$_{29-38}$ peptide, 293-A2 cells pulsed with HPV 16 E711-19 peptide, 293-A2 cells transduced with a plasmid encoding HPV 16 E6, 293-A2 cells transduced with a plasmid encoding GFP, 293-A2 cells, retrovirus-transduced 624 cells stably expressing HPV 16 E7 (624-E7), retrovirus-transduced 624 cells stably expressing HPV 16 E6 (624-E6), SCC152 cells, SCC90 cells, CaSki cells, HPV-18 cervical cancer cells, melanoma control cells, 624 cells, or SiHa cells. IFN-γ was measured. The results are shown in FIG. 5. As shown in FIG. 5, CD8 positive and CD4 positive PBMC transduced with a recombinant expression vector encoding the amino acid sequences of SEQ ID NOs: 17 and 18 both specifically recognize HPV 16-positive tumor cell lines and other HLA-A2$^+$HPV16$^+$ targets in an HLA-A2-restricted manner.

Example 6

This example demonstrates that cells transduced with a recombinant expression vector encoding the amino acid sequences of SEQ ID NOs: 17 and 18 demonstrate avid recognition of HPV 16 E6$_{29-38}$-pulsed T2 cells.

Figure 6A:
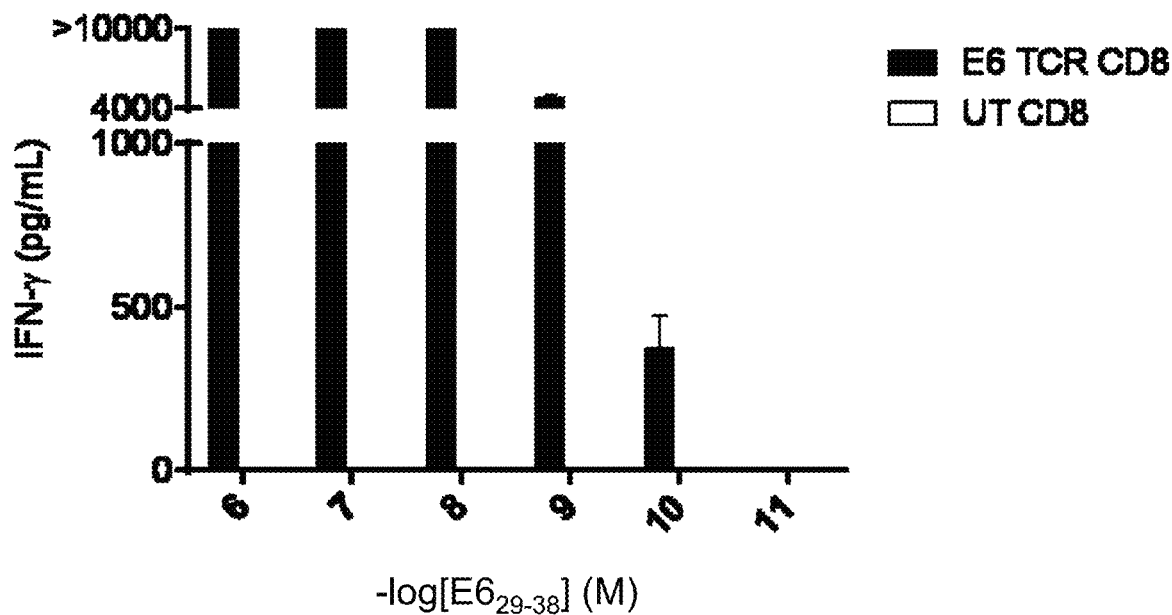
FIG. 6A is a bar graph showing IFN-γ (pg/mL) secreted by untransduced (UT) CD8-positive PBL (unshaded bars) or CD8 positive PBL transduced with a nucleotide sequence encoding SEQ ID NOs: 17 and 18 (shaded bars) upon co-culture with target T2 cells pulsed with varying concentrations of E6$_{29-38}$ peptide (−log M).
Figure 6B:
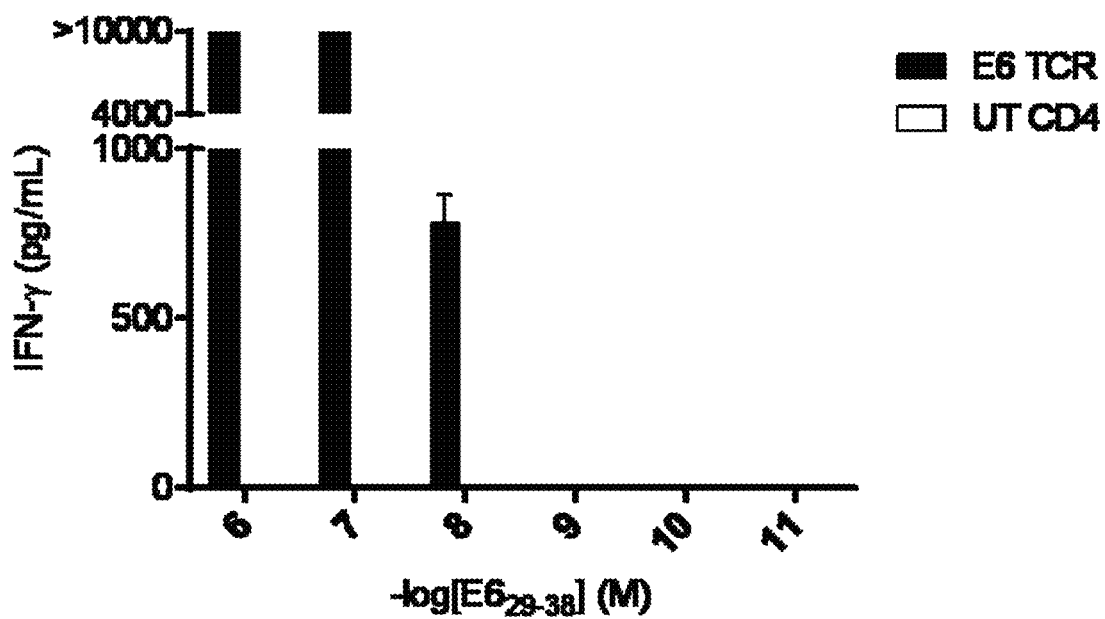
FIG. 6B is a bar graph showing IFN-γ (pg/mL) secreted by untransduced CD4-positive PBL (unshaded bars) or CD4 positive PBL transduced with a nucleotide sequence encoding SEQ ID NOs: 17 and 18 (E6 TCR; shaded bars) upon co-culture with target T2 cells pulsed with varying concentrations of E6$_{29-38}$ peptide (−log M).

CD8-positive or CD4-positive PBL were not transduced (untransduced) or transduced with the expression vector of Example 2 and were co-cultured with target T2 cells pulsed with varying concentrations of HPV 16 E6$_{29-38}$ peptide. IFN-γ was measured. The results are shown in FIGS. 6A and 6B. As shown in FIGS. 6A and 6B, CD4 positive and CD8 positive cells transduced with a recombinant expression vector encoding the amino acid sequences of SEQ ID NOs: 17 and 18 demonstrated avid recognition of HPV 16 E6$_{29-38}$-pulsed T2 cells.

Example 7

This example demonstrates a method of treating HPV 16' cancer in a human patient, comprising administering to the patient autologous T cells transduced to express an anti-HPV 16 E6$_{29-38}$ TCR comprising the amino acid sequences of SEQ ID NOs: 17 and 18.

Patients will have recurrent/refractory or metastatic HPV-16$^+$ cancer. A sample of cancerous tissue will be tested for HPV 16 genotype by in situ hybridization (ISH) or PCR. Patients will also be tested for HLA-A2 expression. The patients will have had a prior first line treatment for recurrent/refractory or metastatic disease, or the patient will have declined standard therapy.

Patients will be treated with cyclophosphamide (60 mg/kg/day intravenously (IV)) on days −7 and −6 and fludarabine (25 mg/m2/day IV) on days −5 through −1. Autologous PBMC will be transduced with the MSGV1 expression vector of Example 2. The numbers of transduced cells will be rapidly expanded as previously described (Dudley et al. *J. Immunother.* 26:332-42 (2003) and Riddell et al. *J. Immunol. Methods* 128:189-201 (1990)). Briefly, cells will be cultured with irradiated (40 Gy) allogeneic peripheral blood mononuclear "feeder" cells in complete medium (CM) with 30 ng/mL anti-CD3 antibody and 6000 IU/mL IL-2. Expanded numbers of transduced cells will be administered to the patients along with a high dose of interleukin (IL)-2 on day 0.

Objective tumor responses will be evaluated according to RECIST (Response Evaluation Criteria In Solid Tumors) 1.0. If at least three out of 18 patients respond to treatment at four months or more after treatment, the cohort will be expanded to 35 patients. Toxicity will also be evaluated. Immunological studies (including, for example, expansion, persistence, phenotype, and function of the infused cells) will also be studied.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of producing an engineered population of human cells, the method comprising:
   introducing a recombinant expression vector to an isolated population of human cells, wherein the recombinant expression vector comprises a nucleotide sequence encoding a TCR having antigenic specificity for HPV 16 E6 and comprising the alpha chain CDR1 amino acid sequence of SEQ ID NO: 3, the alpha chain CDR2 amino acid sequence of SEQ ID NO: 4, the alpha chain CDR3 amino acid sequence of SEQ ID NO: 5, the beta chain CDR1 amino acid sequence of SEQ ID NO: 6, the beta chain CDR2 amino acid sequence of SEQ ID NO: 7, and the beta chain CDR3 amino acid sequence of SEQ ID NO: 8.

2. The method of claim 1, wherein the TCR has antigenic specificity for HPV 16 E6$_{29-38}$ comprising the amino acid sequence of SEQ ID NO: 2.

3. The method of claim 1, wherein the TCR comprises a human variable region and a murine constant region.

4. The method of claim 1, wherein the TCR comprises the amino acid sequences of SEQ ID NOs: 9 and 10.

5. The method of claim 1, wherein the isolated population of human cells is an isolated population of human peripheral blood lymphocytes.

6. The method of claim 1, wherein the isolated population of human cells is an isolated population of human peripheral blood mononuclear cells.

7. The method according to claim 1, wherein the nucleotide sequence is codon-optimized.

8. A method of producing an engineered population of human cells, the method comprising:
   introducing a recombinant expression vector to an isolated population of human cells, wherein the recombinant expression vector comprises a nucleotide sequence encoding a polypeptide comprising a functional portion of a TCR, wherein the functional portion of the TCR comprises the alpha chain CDR1 amino acid sequence of SEQ ID NO: 3, the alpha chain CDR2 amino acid sequence of SEQ ID NO: 4, the alpha chain CDR3 amino acid sequence of SEQ ID NO: 5, the beta chain CDR1 amino acid sequence of SEQ ID NO: 6, the beta chain CDR2 amino acid sequence of SEQ ID NO: 7, and the beta chain CDR3 amino acid sequence of SEQ ID NO: 8, and has antigenic specificity for human papillomavirus (HPV) 16 E6.

9. The method of claim 8, wherein the polypeptide comprises the amino acid sequences of SEQ ID NOs: 9 and 10.

10. The method of claim 8, wherein the polypeptide comprises the amino acid sequences of SEQ ID NOs: 17 and 18.

11. The method of claim 8, wherein the isolated population of human cells is an isolated population of human peripheral blood lymphocytes.

12. The method of claim 8, wherein the isolated population of human cells is an isolated population of human peripheral blood mononuclear cells.

13. The method according to claim 8, wherein the nucleotide sequence is codon-optimized.

14. A method of producing an engineered population of human cells, the method comprising:
introducing a recombinant expression vector to an isolated population of human cells, wherein the recombinant expression vector comprises a nucleotide sequence encoding a protein comprising a TCR or a functional portion thereof, wherein the TCR or the functional portion thereof comprises a first polypeptide chain comprising the alpha chain CDR1 amino acid sequence of SEQ ID NO: 3, the alpha chain CDR2 amino acid sequence of SEQ ID NO: 4, the alpha chain CDR3 amino acid sequence of SEQ ID NO: 5 and a second polypeptide chain comprising the beta chain CDR1 amino acid sequence of SEQ ID NO: 6, the beta chain CDR2 amino acid sequence of SEQ ID NO: 7, and the beta chain CDR3 amino acid sequence of SEQ ID NO: 8, and has antigenic specificity for human papillomavirus (HPV) 16 E6.

15. The method according to claim 14, wherein the first polypeptide chain comprises the amino acid sequence of SEQ ID NO: 9 and the second polypeptide chain comprises the amino acid sequence of SEQ ID NO: 10.

16. The method of claim 14, wherein the first polypeptide chain comprises the amino acid sequence of SEQ ID NO: 17 and the second polypeptide chain comprises the amino acid sequence of SEQ ID NO: 18.

17. The method according to claim 14, wherein the nucleotide sequence is codon-optimized.

18. The method of claim 14, wherein the isolated population of human cells is an isolated population of human peripheral blood lymphocytes.

19. The method of claim 14, wherein the isolated population of human cells is an isolated population of human peripheral blood mononuclear cells.

* * * * *